(12) United States Patent
Tanaka et al.

(10) Patent No.: US 10,884,231 B2
(45) Date of Patent: Jan. 5, 2021

(54) ILLUMINATION DEVICE AND ENDOSCOPE APPARATUS INCLUDING THE ILLUMINATION DEVICE

(71) Applicant: OLYMPUS CORPORATION, Tokyo (JP)

(72) Inventors: Yoshinori Tanaka, Hino (JP); Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/690,195

(22) Filed: Nov. 21, 2019

(65) Prior Publication Data
US 2020/0088988 A1 Mar. 19, 2020

Related U.S. Application Data

(63) Continuation of application No. PCT/JP2017/019267, filed on May 23, 2017.

(51) Int. Cl.
*G02B 23/24* (2006.01)
*G02B 6/26* (2006.01)
(Continued)

(52) U.S. Cl.
CPC ...... *G02B 23/2469* (2013.01); *A61B 1/00177* (2013.01); *A61B 1/0661* (2013.01);
(Continued)

(58) Field of Classification Search
CPC .............. G92B 23/2469; G92B 6/0008; G92B 23/2423; F21V 9/30; F21V 9/20; A61B 1/0661; A61B 1/00177
See application file for complete search history.

(56) References Cited

U.S. PATENT DOCUMENTS

2018/0277720 A1* 9/2018 Zheng ................ C09K 11/0883

FOREIGN PATENT DOCUMENTS

JP 2005-328921 A 12/2005
JP 4689190 B2 5/2011
(Continued)

OTHER PUBLICATIONS

English translation of International Preliminary Report on Patentability dated Dec. 5, 2019, together with the Written Opinion received in related International Application No. PCT/JP2017/019267.

(Continued)

*Primary Examiner* — Joseph L Williams
(74) *Attorney, Agent, or Firm* — Scully, Scott, Murphy & Presser, P.C.

(57) ABSTRACT

An illumination device includes a light converter that primary light enters and that is configured to convert at least part of the primary light into secondary light having a second wavelength that differs from a first wavelength of the primary light and to diffuse the secondary light, a first reflector configured to reflect at least part of the diffused secondary light toward the light converter, and a holder holding at least one of the first reflector and the light converter. The first reflector and the light converter are separated from each other so that the primary light transmitted through the first reflector enters the light converter.

20 Claims, 12 Drawing Sheets

(51) Int. Cl.
| | |
|---|---|
| *F21V 9/20* | (2018.01) |
| *F21V 9/30* | (2018.01) |
| *A61B 1/06* | (2006.01) |
| *A61B 1/00* | (2006.01) |
| *F21V 8/00* | (2006.01) |
| *F21Y 115/30* | (2016.01) |

(52) U.S. Cl.
CPC ............... *F21V 9/20* (2018.02); *F21V 9/30* (2018.02); *G02B 6/0008* (2013.01); *G02B 23/2423* (2013.01); *F21Y 2115/30* (2016.08)

(56) References Cited

FOREIGN PATENT DOCUMENTS

| | | |
|---|---|---|
| JP | 2015-019013 A | 1/2015 |
| JP | 2015-211727 A | 11/2015 |

OTHER PUBLICATIONS

International Search Report dated Sep. 5, 2017 issued in PCT/JP2017/019267.
English Abstract of JP 2005328921 A, dated Dec. 2, 2005.

\* cited by examiner

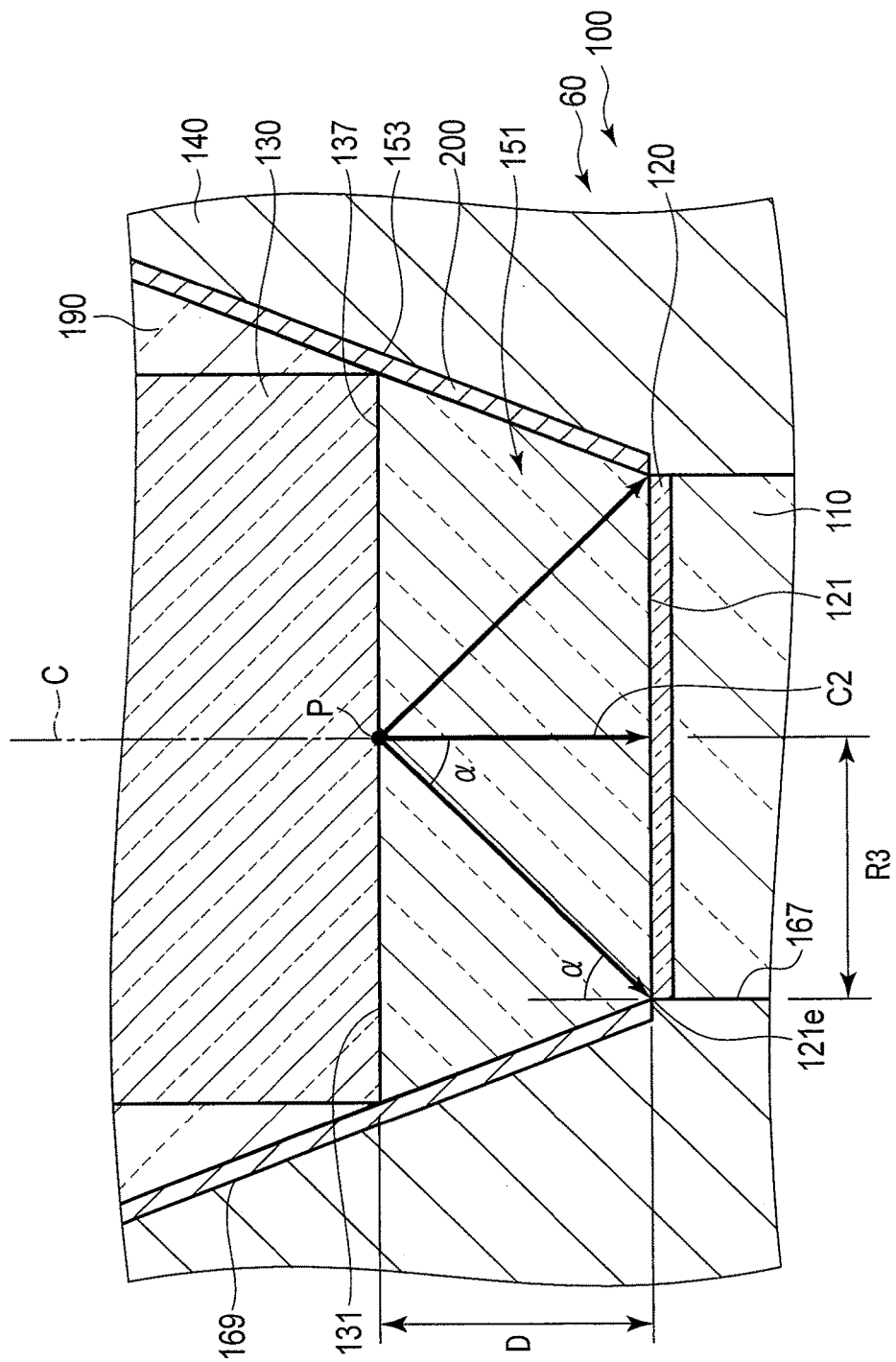
F I G. 3D

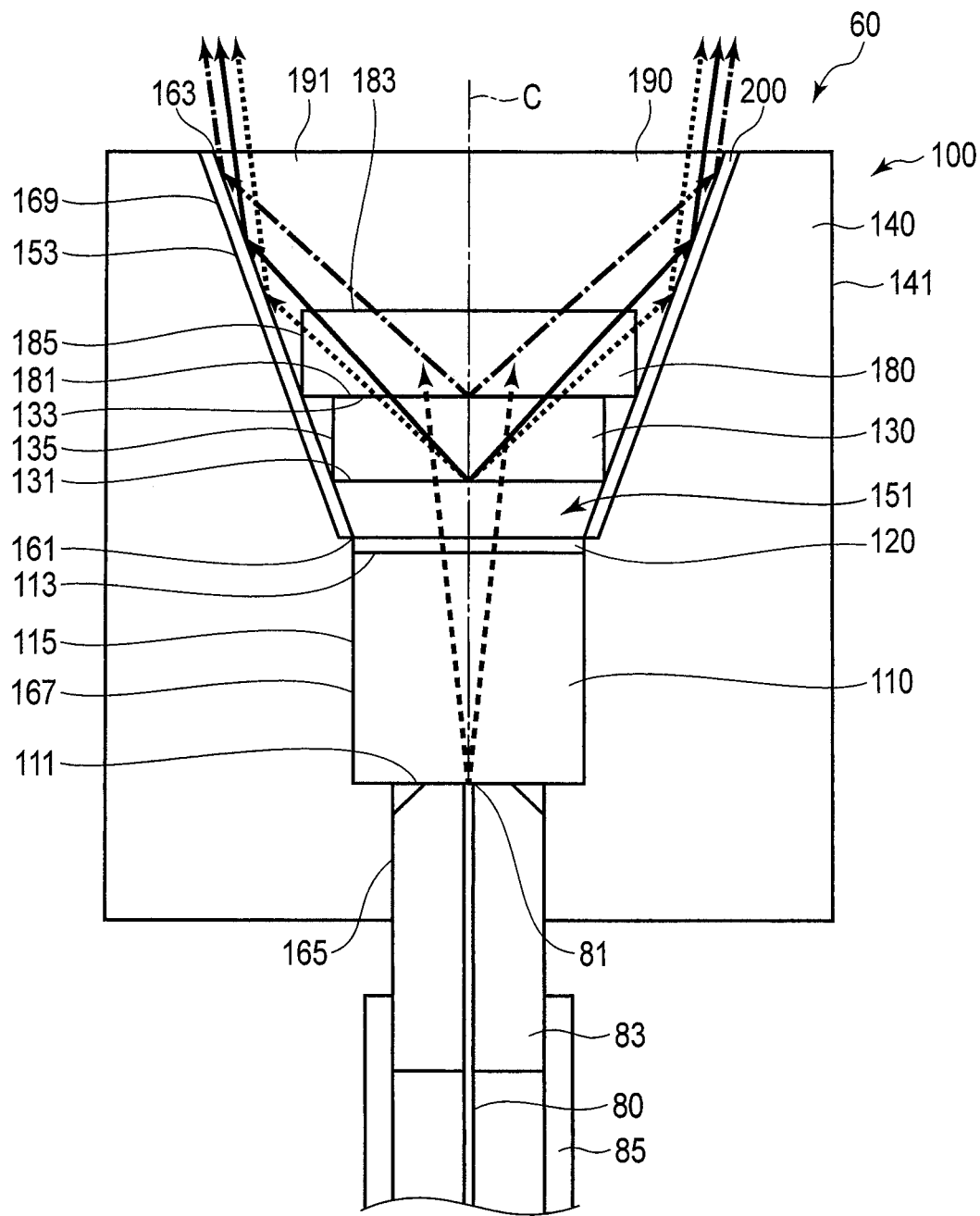
·····▶ Primary light
——▶ Wavelength-converted light (secondary light)
······▶ First diffused light (secondary light)
－－▶ Second diffused light (tertiary light)
F I G. 4A

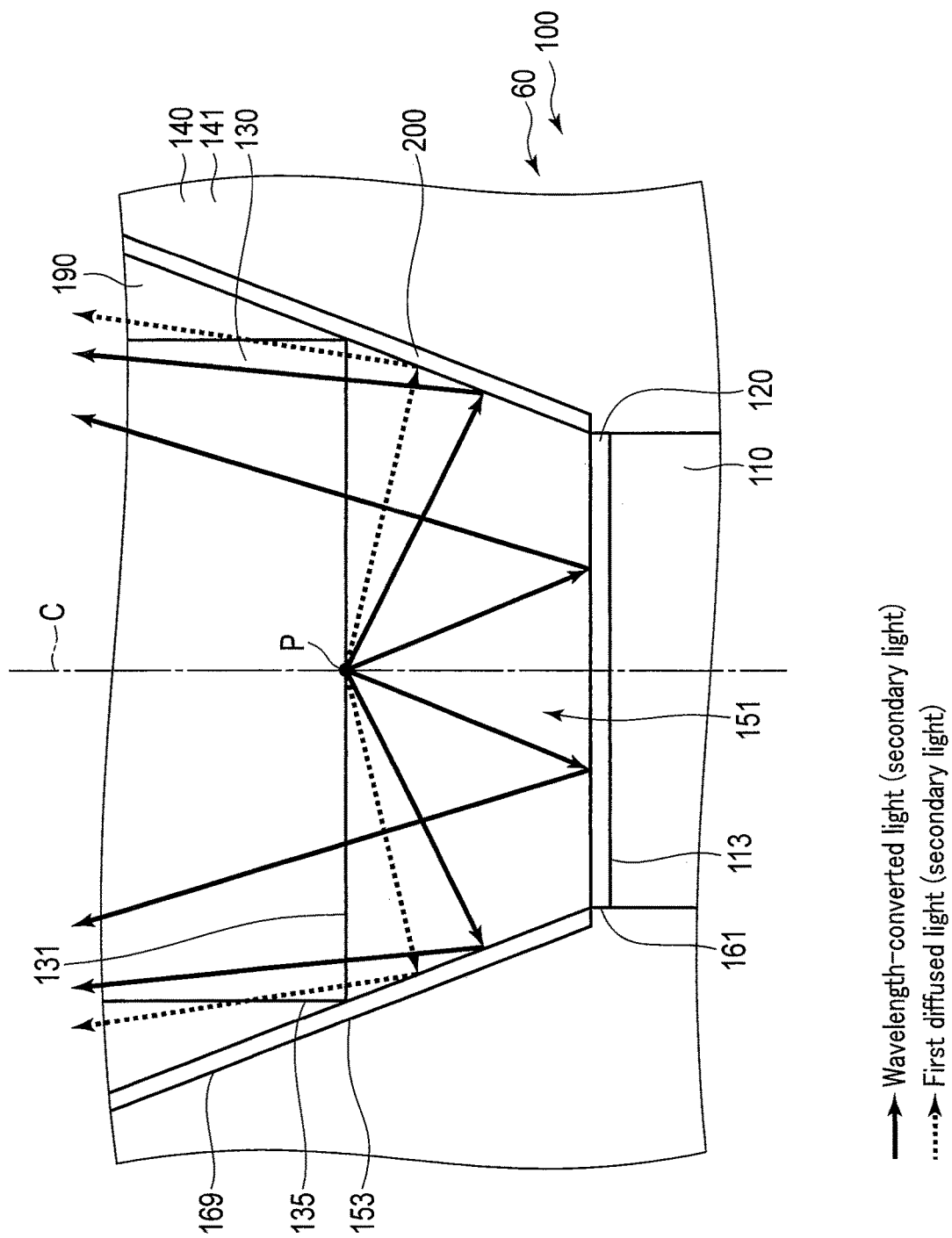
F I G. 4B

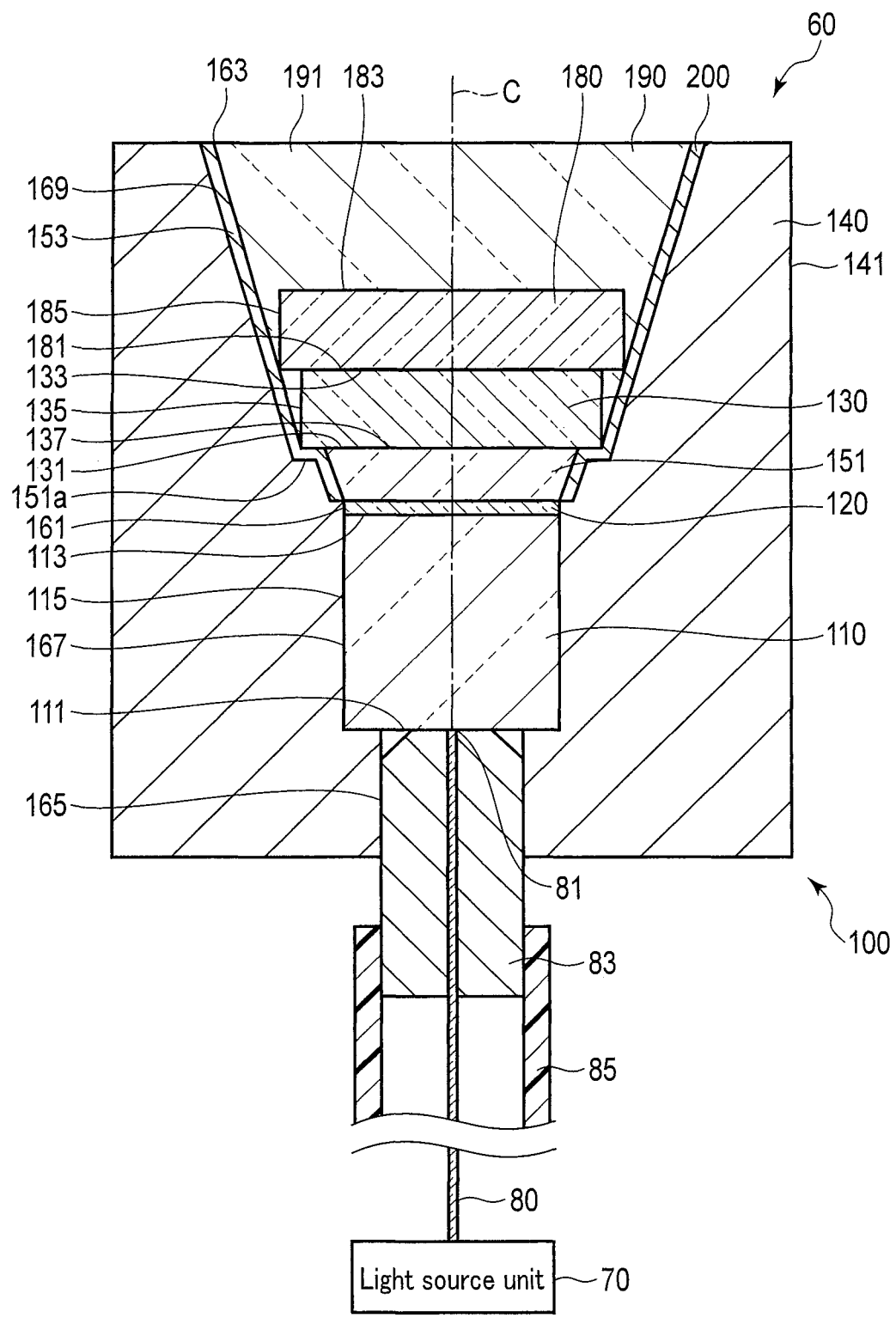
F I G. 6

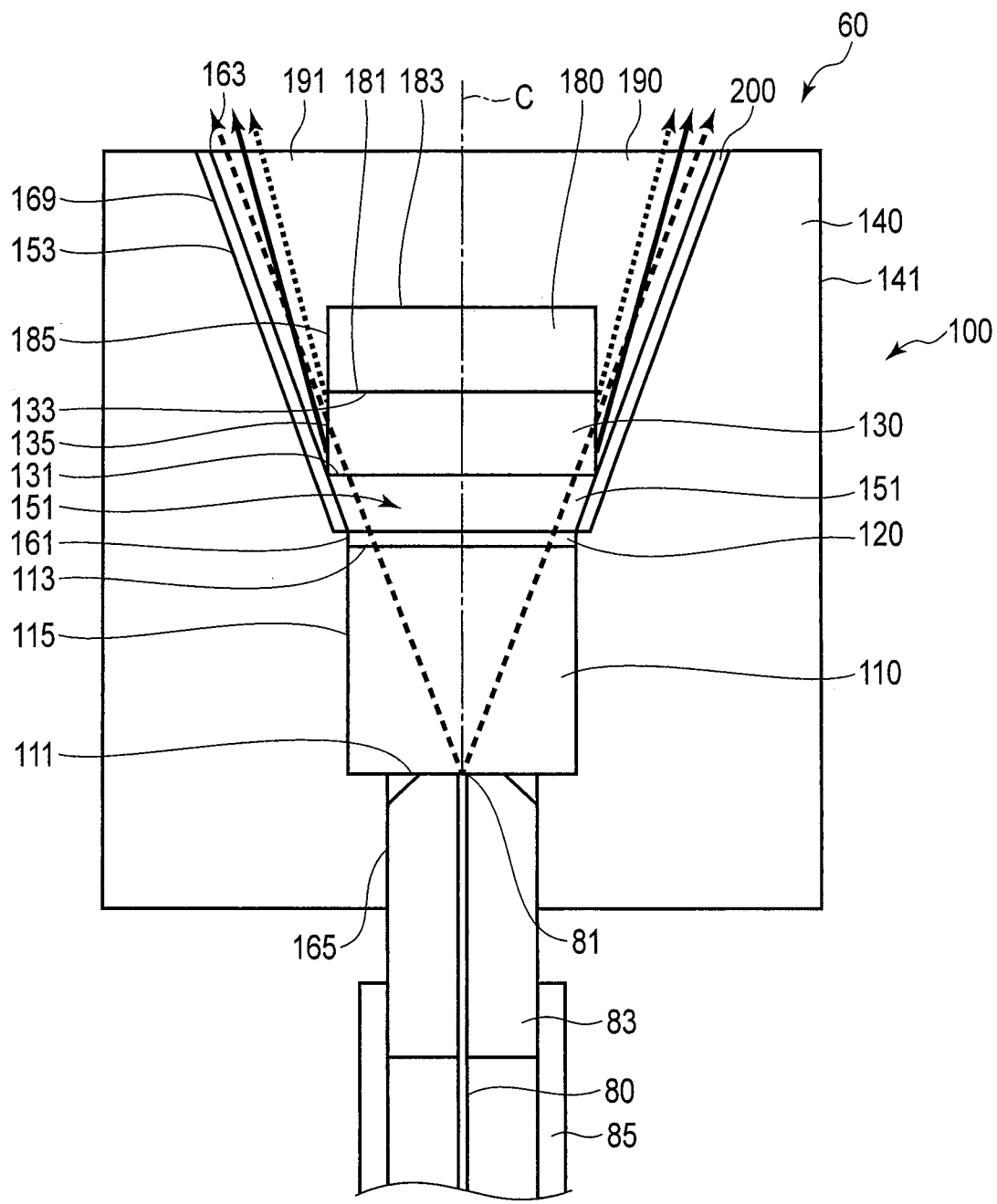
F I G. 8

ILLUMINATION DEVICE AND ENDOSCOPE APPARATUS INCLUDING THE ILLUMINATION DEVICE

CROSS-REFERENCE TO RELATED APPLICATIONS

This application is a Continuation Application of PCT Application No. PCT/JP2017/019267, filed May 23, 2017, the entire contents of which are incorporated herein by reference.

BACKGROUND OF THE INVENTION

1. Field of the Invention

The present invention relates to an illumination device and an endoscope apparatus including the illumination device.

2. Description of the Related Art

For example, Japanese Patent No. 4689190 discloses an endoscope apparatus having an optical fiber exit end portion, a fluorescent member, and a fluorescent reflection film, disposed in a distal end portion of an insertion section. The optical fiber exit end portion emits excitation light, which is primary light, toward the fluorescent member. The fluorescent member includes a high-refractive-index medium having a refractive index that is higher than that of air, and granular fluorescent substances dispersed in the high-refractive-index medium and emitting fluorescence as secondary light based on the primary light. The fluorescent member is disposed on the distal-end side of the insertion section that is located in front of the optical fiber exit end portion. The fluorescent reflection film is disposed between the optical fiber emit end portion and the fluorescent member.

The primary light is emitted from the optical fiber exit end portion, transmitted through the fluorescent reflection film, and enters the fluorescent member. The fluorescent member generates fluorescence, which is secondary light, based on the primary light, and emits part of the fluorescence as illumination light to the front that is opposite to the optical fiber exit end portion. The illumination light is then emitted toward the outside from the distal end portion of the insertion section. The remaining part of the fluorescence returns (travels) to the fluorescent reflection film from the fluorescent member as return light.

The fluorescent reflection film reflects the remaining part of the fluorescence, which returns to the fluorescent reflection film from the fluorescent member, toward the fluorescent member. The reflected fluorescence is emitted as illumination light from the distal end portion of the insertion section toward the outside.

In the endoscope apparatus, therefore, an observation target can efficiently be illuminated with illumination light.

BRIEF SUMMARY OF THE INVENTION

An illumination device according to the present invention includes a light converter that primary light enters and that is configured to convert at least part of the primary light into secondary light having a second wavelength that differs from a first wavelength of the primary light and to diffuse the secondary light, a first reflector configured to reflect at least part of the diffused secondary light toward the light converter, and a holder holding at least one of the first reflector and the light converter with the first reflector and the light converter being separated from each other so that the primary light transmitted through the first reflector enters the light converter.

An endoscope apparatus including the illumination device according to the present invention includes a light converter that primary light enters and that is configured to convert at least part of the primary light into secondary light having a second wavelength that differs from a first wavelength of the primary light and to diffuse the secondary light, a first reflector configured to reflect at least part of the diffused secondary light toward the light converter, a holder holding at least one of the first reflector and the light converter with the first reflector and the light converter being separated from each other so that the primary light transmitted through the first reflector enters the light converter, and an endoscope configured to emit illumination light generated based on the primary light.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3D is a diagram illustrating a relationship among an incident angle, the index value, and the relative distance.

FIG. 4A is a diagram schematically showing primary light, wavelength-converted light (secondary light), first diffused light (secondary light), and second diffused light (tertiary light), which travel forward in a holding unit of an illumination unit disposed in the illumination device.

FIG. 4B is a diagram schematically showing wavelength-converted light (secondary light) and first diffused light (secondary light) as return light that returns to a first reflection member from a light converting member in the holding unit shown in FIG. 4A.

FIG. 6 is a diagram schematically showing an illumination device of a second embodiment.

FIG. 8 is a diagram schematically showing primary light, wavelength-converted light (secondary light), and first diffused light (secondary light), which travel forward in a holding unit of an illumination device of a fourth embodiment.

DETAILED DESCRIPTION OF THE INVENTION

Each of the embodiments of the present invention will be described below with reference to the drawings. In some drawings, some of the members are omitted for clarity of the drawings.

Figure 2:
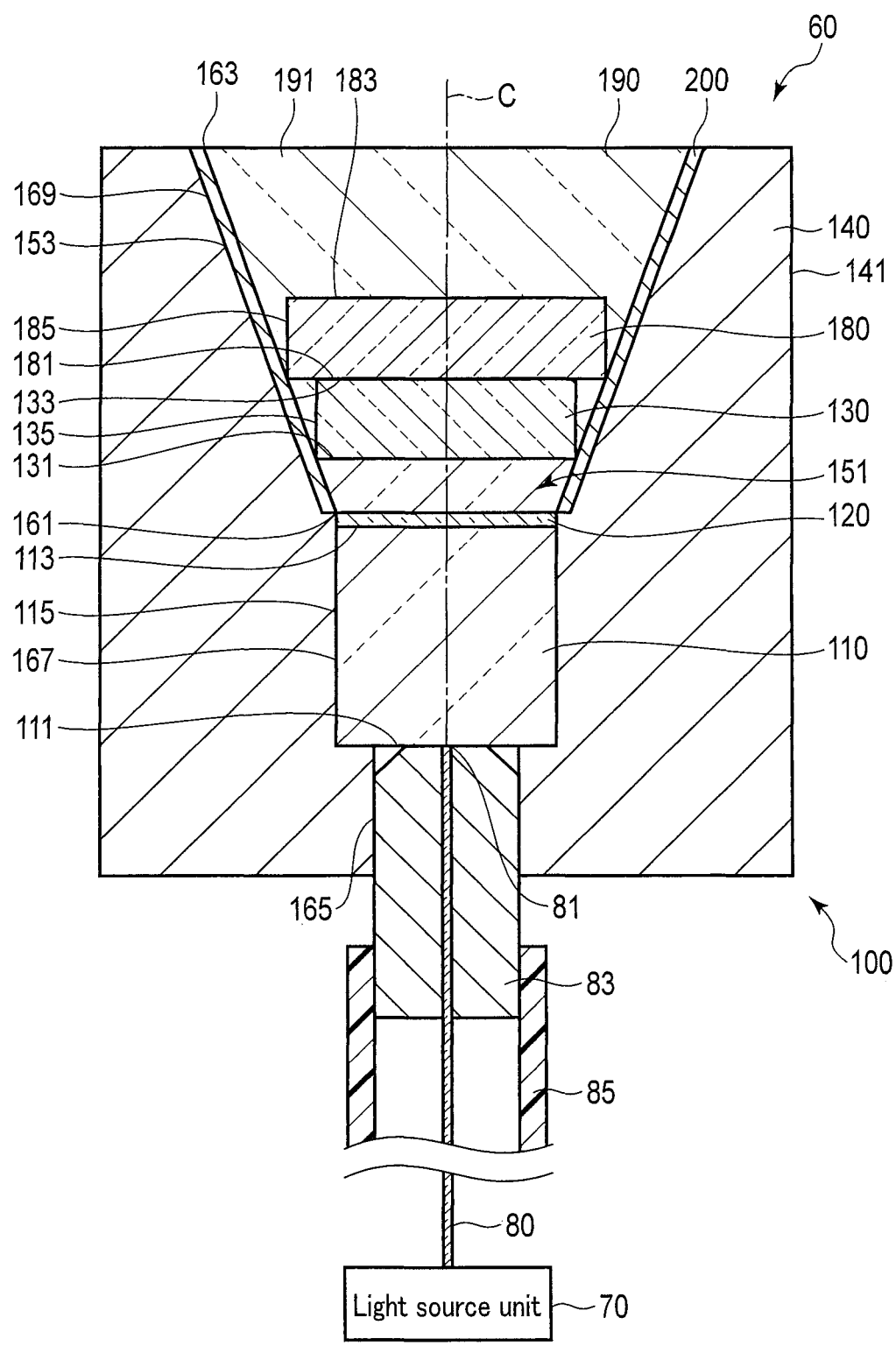
FIG. 2 is a diagram schematically showing the illumination device of the first embodiment.

As shown in FIG. 2, the central axis of primary light traveling from a first reflection member 120 as a reflector to a light converting member 130 as a light converter will be referred to as central axis C. The direction of the central axis C indicates a direction from the first reflection member 120 toward the light converting member 130, such as a direction from the lower side to the upper side in FIG. 2. In the direction of the central axis C, the side closer to a light source unit 70 will be referred to as the back, and the side closer to an illumination unit 100 will be referred to as the front.

An illumination device 60 as shown in FIG. 2, which is an example of an illumination device for endoscopes, mounted on an endoscope 20 of an endoscope system 10 shown in FIG. 1, will be described. The endoscope 20 is an example of a small-sized precision instrument. The small-sized precision instrument includes a microscope, an illumination probe, etc. in addition to the endoscope 20. For example, the illumination device 60 may be mounted on a microscope or an illumination probe, or may function as a device alone.

First Embodiment

A first embodiment of the present invention will be described below.

Figure 1:
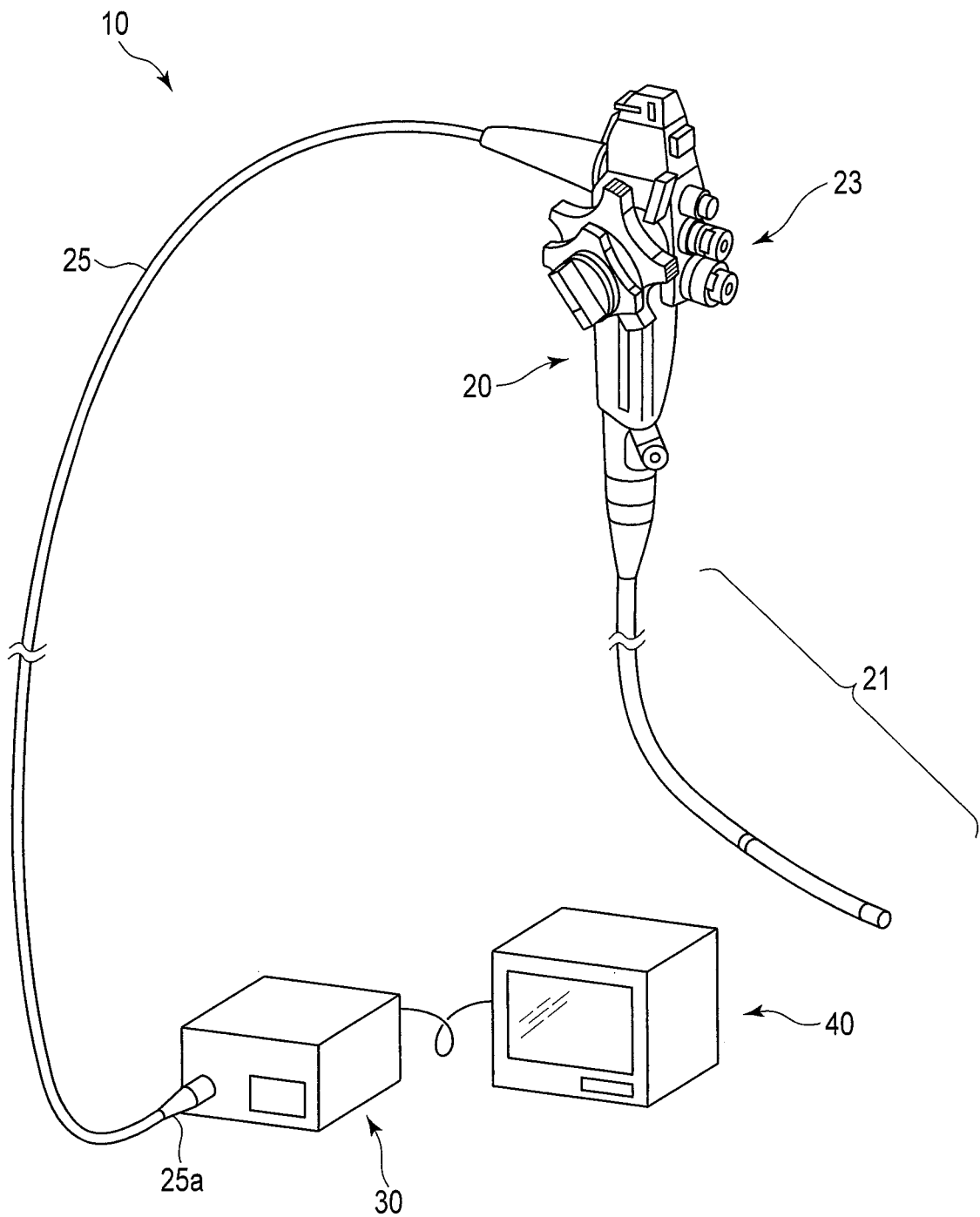
FIG. 1 is a schematic view of an endoscope system including an illumination device of a first embodiment of the present invention.

The endoscope system 10 as shown in FIG. 1 is installed in a laboratory, an operating room, and the like. The endoscope system 10 includes an endoscope 20 configured to illuminate an observation target in a tubular section, such as a lumen of a patient, with illumination light to image the observation target, a control device 30 detachably connected to the endoscope 20 and configured to control the entire endoscope system 10 including the endoscope 20, and a display device 40 connected to the control device 30. The observed target is, for example, an affected part and a lesion.

The control device 30 includes an image processing unit (not shown) configured to perform image processing on an image of the observation target, which is imaged by an imaging unit (not shown) of the endoscope 20. The image processing unit is configured by a hardware circuit including, for example, an ASIC. The image processing unit may be configured by a processor. When the image processing unit is configured by a processor, an external memory or an internal memory (not shown), which is accessible by the processor, is disposed in the control device 30. The internal memory or the external memory stores a program code that causes the processor to function as an image processing unit when the processor executes the program code.

The display device 40 includes, for example, a monitor configured to display an image processed by the image processing unit.

The endoscope 20 functions as, for example, an insertion device to be inserted into a tubular section. The endoscope 20 may be a front-viewing endoscope or a side-viewing endoscope.

The endoscope 20 of the present embodiment will be described as, for example, a medical endoscope, but need not be limited thereto. The endoscope 20 may be an industrial endoscope that is inserted into a tubular section of an industrial product such as a pipe or may be an insertion instrument such as a catheter including only the illumination device 60.

As shown in FIG. 1, the endoscope 20 includes a hollow elongated insertion section 21 to be inserted into a tubular section and a control section 23 coupled to a proximal end portion of the insertion section 21 and gripped by an operator to operate the endoscope 20. The endoscope 20 includes a universal cord 25 connected to the control section 23 and extending from the side surface of the control section 23.

The insertion section 21 of the present embodiment is, for example, a flexible endoscope that can flexibly be bent over the entire length of the insertion section 21. Note that the insertion section 21 may be a rigid endoscope in which the entire insertion section 21 is not bent or may be a rigid endoscope in which only a part of the insertion section 21 can flexibly be bent.

The insertion section 21 includes an imaging element (not shown) of the imaging unit. The imaging element is disposed in the interior of the distal end portion of the insertion section 21. The imaging element images light reflected from the observation target illuminated with illumination light emitted from the illumination unit 100. Then, the imaging element outputs the reflected light as an electrical signal to the image processing unit through a signal cable (not shown). The imaging element includes a CCD, a CMOS, or the like.

As shown in FIG. 1, the universal cord 25 includes a connecting portion 25a detachably attached to the control device 30. The connecting portion 25a connects the endoscope 20 detachably to the control device 30. The connecting portion 25a is provided to transfer data between the endoscope 20 and the control device 30.

In the endoscope system 10, the endoscope 20 is directly connected to the control device 30 through the universal cord 25 including the connecting portion 25a. However, although not shown, the universal cord 25 may be omitted, and the endoscope 20 may be of a wireless type. In this case, the endoscope 20 is connected to the control device 30 by a radio signal.

The endoscope 20 includes the illumination device 60 (see FIG. 2) configured to emit illumination light from the distal end portion of the insertion section 21 to the front of the insertion section 21 and to the outside thereof. The illumination device 60 includes a light source unit 70 configured to emit primary light and a light guide 80 configured to guide the primary light emitted from the light source unit 70. The illumination device 60 includes an illumination unit 100 optically connected to the light source unit 70 through the light guide 80 to receive the primary light guided by the light guide 80.

The light source unit 70 is provided, for example, in the interior of the control section 23. The light source unit 70 includes a light source (not shown) configured to emit primary light as excitation light having high coherence. This light source is, for example, a laser diode (not shown) configured to emit laser light. The color of the laser light is, for example, blue. The center wavelength of the blue laser light is, for example, 445 nm. The center wavelength of the laser light need not be limited thereto. The light source unit 70 includes a lens (not shown) that is disposed in front of the light source. The lens causes the primary light emitted from the light source to converge on the light guide 80. The light source unit 70 includes a receptacle (not shown) to which the light guide 80 is optically connected. Note that the light source unit 70 is not limited to the receptacle but may be a pigtail. The light source unit 70 may be built in, for example, the control device 30. Therefore, the illumination device 60 may be mounted on the endoscope system 10, and the mounting position of the illumination device 60 is not particularly limited.

The light guide 80 is optically connected to the light source unit 70 and the illumination unit 100 to guide, to the illumination unit 100, the primary light emitted from the light source unit 70. The light guide 80 is shaped like a column, such as a cylinder. The light guide 80 is disposed, for example, in the interior of the control section 23 and the insertion section 21. The light guide 80 can be bent as desired. The light guide 80 is, for example, a single-line optical fiber and its core diameter is, for example, 50 μm and its numerical aperture NA is, for example, 0.2. The optical fiber is a multimode optical fiber. The core diameter or the numerical aperture NA is not particularly limited to the value. The optical fiber is formed of, for example, glass, or plastic. The optical fiber may be, for example, a multimode fiber of quartz. The light guide 80 may be a bundle fiber. The light guide 80 is an elongated member that can be bent by an external force. The exit end face 81 of the light guide 80 has a section perpendicular to the central axis of a core (not shown) of the light guide 80. The exit end face 81 is polished or cleaved. The exit end face 81 is, for example, a plane. The exit end face 81 is disposed at the exit end portion of the light guide 80 and is optically connected to the illumination unit 100. The exit end face 81 emits primary light toward the illumination unit 100. The exit end portion of the light guide 80 is an end portion opposed to the light source unit 70.

The exit end portion of the light guide 80, including the exit end face 81, is inserted into and engaged with a ferrule 83 and is protected by the ferrule 83. The distal end portion of the ferrule 83, including the exit end portion, is inserted into a first hollow portion 165 (described later) of the illumination unit 100 so that the exit end face 81 is optically connected to the illumination unit 100. The distal end face of the ferrule 83 is planar and is disposed on the same plane as the exit end face 81.

Most of the light guide 80, excluding the exit end portion of the light guide 80, is inserted into a protection member 85. The protection member 85 is shaped like a column, such as a cylinder. The protection member 85 is, for example, a tube. When the light guide 80 is inserted into the protection member 85, the protection member 85 covers the outer periphery of the light guide 80. The protection member 85 is disposed in the insertion section 21 and covers the light guide 80 in the insertion section 21. Although not shown, the protection member 85 may be disposed in the control section 23 and extend from the insertion section 21 to the periphery of the light source unit 70 to cover the light guide 80 in the control section 23. The protection member 85 is of, for example, resin, and can be bent as desired. The protection member 85 protects the light guide 80 in order to improve the mechanical strength of the light guide 80, such as tensile resistance and bending resistance and to prevent the light guide 80 from breaking.

The inner peripheral surface of the protection member 85 is separated from the outer peripheral surface of the light guide 80, and a gap is formed between the protection member 85 and the light guide 80. If the light guide 80 can be bent along with the bending of the insertion section 21, an intervening member (not shown) such as resin may be disposed in the gap. Thus, the mechanical strength of the light guide 80 can be further improved by the intervening member. The intervening member may be filled in the gap. The intervening member may be omitted, and the inner peripheral surface of the protection member 85 may be in close contact with the outer peripheral surface of the light guide 80.

The inner peripheral surface of the distal end portion of the protection member 85 is in close contact with the outer peripheral surface of the proximal end portion of the ferrule 83 disposed outside the illumination unit 100. The inner peripheral surface may be bonded to the outer peripheral surface.

The ferrule 83 may be omitted or may be inserted into the first hollow portion 165 with the exit end portion exposed from the protection member 85. In this case, the exit end portion is fixed to the illumination unit 100 by an adhesive or the like (not shown).

The illumination unit 100 is disposed at an exit end portion of the light guide 80 disposed on the side opposed to the light source unit 70, and is optically connected to the exit end portion. The illumination unit 100 is disposed in the interior of the distal end portion of the insertion section 21. The illumination unit 100 is adjacent to the imaging element, for example, in the radial direction of the insertion section 21.

The illumination unit 100 receives the primary light emitted from the exit end face 81. The illumination unit 100 emits illumination light generated on the basis of the primary light. Specifically, the illumination unit 100 generates secondary light by converting at least some of the optical properties of the primary light. The secondary light has optical properties that differ from those of the primary light. The optical properties include, for example, at least one of a wavelength and a light distribution angle. For example, the illumination unit 100 absorbs part of the primary light and converts the absorbed primary light into secondary light that is wavelength-converted light having a wavelength range that differs from that of the primary light. For example, the illumination unit 100 converts different part of the primary light into secondary light that is first diffused light with low coherence, by increasing the spread angle of the primary light and diffusing the primary light, without changing the wavelength of the primary light. The illumination unit 100 also converts part of at least one of the primary light, wavelength-converted light (secondary light), and first diffused light (secondary light) into tertiary light that is second diffused light with low coherence, by increasing the spread angle of the part and diffusing the part, without changing the wavelength of the part. The illumination unit 100 emits the primary light, secondary light, and tertiary light as illumination light. The illumination light may include light (e.g. secondary light or tertiary light) having optical properties that differ from those of the primary light. That is, the illumination light may include at least light other than the primary light (e.g. secondary light or tertiary light).

In order to illuminate an observation target with illumination light, the illumination unit 100 emits the illumination light toward the side opposed to the light source unit 70. For example, the illumination unit 100 emits illumination light to the outside of the illumination unit 100. The outside of the illumination unit 100 corresponds to the front of the insertion section 21 and the outside thereof. Specifically, the illumination unit 100 emits illumination light from a holder exit portion 163 (described later) toward the front of the holder exit portion 163. The front of the insertion section 21 and the front of the holder exit portion 163 correspond to, for example, the upper side of FIG. 2, which is opposite to the positions in which the light source unit 70 and the light guide 80 are disposed in the direction of the central axis C. Therefore, the illumination light means light emitted from the illumination unit 100 to the outside of the illumination unit 100.

The illumination unit 100 includes a transmission member 110, a first reflection member 120, a light converting member 130, a holding unit 140 as a holder, a diffusing member 180, a transparent member 190, and a second reflection member 200. The transmission member 110, first reflection member 120, light converting member 130, holding unit 140, diffusing member 180, transparent member 190, and second reflection member 200 are rotationally symmetrical about the central axis C. On the central axis C, the transmission member 110, the first reflection member 120, an orthogonal holding section 151 (described later) of the holding unit 140, the light converting member 130, the diffusing member 180, and the transparent member 190 are arranged in this order from the back to the front.

The transmission member 110 is a member that can transmits the primary light. The transmission member 110 is, for example, glass such as quartz. The transmission member 110 is transparent, for example. The transmission member 110 is shaped like a column, such as a cylinder. The transmission member 110 has a first surface 111 on which the exit end surface 81 and the distal end face of the ferrule 83 abut, a second surface 113 that is a face opposed to the first surface 111, and a peripheral face 115. The first and second surfaces 111 and 113 are planar surfaces having the same area and substantially orthogonal to the central axis C. The peripheral face 115 is disposed between the first and second surfaces 111 and 113.

The first reflection member 120 is disposed between the light source unit 70 and the light converting member 130 and separated from the light source unit 70 and the light converting member 130. For example, the first reflection member 120 is preferably disposed on one-side surface of the transmission member 110. The one-side surface is, for example, the second surface 113 of the transmission member 110. The first reflection member 120 is, for example, disposed over the entire second surface 113. Therefore, the primary light traveling from the back to the front is always transmitted through the first reflection member 120. The first reflection member 120 is a planar member that is substantially orthogonal to the central axis C.

Like the second surface 113 of the transmission member 110, the first reflection member 120 may be disposed on the first surface 111 of the transmission member 110. The first reflection member 120 may be disposed on at least one of the first and second surfaces 111 and 113. The transmission member 110 is disposed in order to position the first reflection member 120, and may be omitted if the first reflection member 120 is positioned. Thus, the first reflection member 120 has only to be disposed between the exit end face 81 and the light converting member 130, apart from the light converting member 130 in the direction of the central axis C.

The first reflection member 120 has a first reflectance for primary light having a first wavelength and a second reflectance for secondary light having at least a second wavelength other than the first wavelength. In the present embodiment, the secondary light includes wavelength-converted light having a wavelength range that differs from that of the primary light and first diffused light having a wavelength range that is substantially the same as that of the primary light and having a light distribution angle that differs from that of the primary light. The first reflection member 120 thus reflects only the wavelength-converted light of the secondary light. The second reflectance is higher than the first reflectance.

Since the first reflectance is extremely low, most of the primary light is transmitted through the first reflection member 120. For example, approximately 95% of the primary light that has reached the first reflection member 120 from the light source unit 70 travels to the light converting member 130 through the first reflection member 120. For example, approximately 5% of the primary light that has reached the first reflection member 120 from the light source unit 70 is reflected and scattered by the first reflection member 120 and returns to the light source unit 70.

The first reflectance also acts on light having the same wavelength as that of the primary light. In the present embodiment, return light that returns (travels) to the first reflection member 120 from the front exists, which will be described in detail later. More specifically, the return light indicates light traveling in a direction opposite to the illumination light in the direction of the central axis C, indicates light traveling from the front to the back, and indicates light traveling toward the light source unit 70. Part of the return light has the same wavelength as that of the primary light. The light having the same wavelength as that of the primary light described above indicates such return light. This return light corresponds to, for example, secondary light as the first diffused light in which the primary light is diffused in the light converting member 130 and tertiary light as the second diffused light in which the primary light is diffused in the diffusing member 180. Here, the first diffused light and the second diffused light are light in which the wavelength of part of the primary light is not changed but the spread angle of the part is increased, the part is diffused and the coherence thereof is lowered. Approximately 95% of the return light having the same wavelength as that of the primary light is transmitted through the first reflection member 120 and travels to the light source unit 70. Approximately 5% of the return light is reflected and scattered by the first reflection member 120 and returns to the front, such as toward the light converting member 130.

The light quantity of the primary light that has reached the first reflection member 120 from the light source unit 70 is much larger than that of the return light that returns to the first reflection member 120 from the front and has the same wavelength as that of the primary light.

Since the second reflectance is much higher than the first reflectance, for example, the first reflection member 120 reflects the secondary light as the wavelength-converted light and the tertiary light as the second diffused light obtained by diffusing the wavelength-converted light. Here, the second diffused light is light in which the wavelength of part of the wavelength-converted light is not changed but the spread angle of the part is increased, the part is diffused, and the coherence thereof is lowered.

The first reflection member 120 has, for example, a plurality of optical thin films. For example, the thin films are dielectric films, and are laminated to each other. The refractive indices of the thin films are different from each other, and a low refractive index layer and a high refractive index layer are formed. Thus, the first reflection member 120 functions as a reflecting film formed on the transmission member 110 and functions as a wavelength filter.

The first reflection member 120 has an incident angle dependency. For example, when the incident angle of the wavelength-converted light (secondary light) as return light with respect to the first reflection member 120 is small, such as approximately 90° with respect to the plane of the first reflection member 120, the transmittance and reflectance wavelength characteristics of the first reflection member 120 are on the longer wavelength side than when the incident angle is large. Since this wavelength corresponds to the wavelength of the wavelength-converted light (secondary light), most of the wavelength-converted light (secondary light) as return light that returns to the first reflection member 120 from the front is reflected forward by the first reflection member 120.

Assume that unlike in the present embodiment, the first reflection member 120 is not separated from but in contact with the light converting member 130. In this case, the incident angle of most of the wavelength-converted light (secondary light) as return light that returns to the first reflection member 120 from the front becomes large. Accordingly, the wavelength-converted light (secondary light) enters the first reflection member 120 and travels inside the first reflection member 120. Then, the optical path length will be lengthened due to the incident angle dependency. For example, when the incident angle is large, such as approximately 45° or more, the transmittance and reflectance wavelength characteristics are shifted to the shorter wavelength side. Therefore, most of the wavelength-converted light (secondary light) as return light that returns to the first reflection member 120 from the front is transmitted through the first reflection member 120 and the transmission member 110 due to the shift. Then, the wavelength-converted light (secondary light) returns to the light source unit 70 through the light guide 80, and is not used as illumination light.

However, in the present embodiment, the first reflection member 120 is separated from the light converting member 130. In the wavelength-converted light (secondary light) as return light whose incident angle with respect to the first reflection member 120 is large, the separation decreases the wavelength-converted light (secondary light) as return light that returns to the first reflection member 120. Accordingly, the transmission of the wavelength-converted light (secondary light) as return light to the first reflection member 120 and the transmission member 110 is reduced, so that the return of the wavelength-converted light (secondary light) to the light source unit 70 is reduced. The separation also increases the wavelength-converted light (secondary light) as return light whose incident angle for the first reflection member 120 is small. Accordingly, the wavelength-converted light (secondary light) as return light that returns to the first reflection member 120 increases. Most of the wavelength-converted light (secondary light) as return light that returns to the first reflection member 120 from the front is reflected toward the light converting member 130 by the first reflection member 120, and is used as illumination light.

The light converting member 130 is disposed in front of the first reflection member 120 and, in other words, it is disposed on the side opposed to the light source unit 70 with respect to the first reflection member 120. The light converting member 130 is disposed away from the first reflection member 120. The light converting member 130 is disposed away from the light source unit 70, and the first reflection member 120 is disposed closer to the light source unit 70 than the light converting member 130. The primary light emitted from the light source unit 70 is transmitted through the first reflection member 120 and then enters the light converting member 130.

The light converting member 130 is shaped like a column, such a cylinder. The light converting member 130 has a first surface 131 that is opposed to the first reflection member 120 and is broader than the first reflection member 120, a second surface 133 that is located opposite to the first surface 131, and a peripheral surface 135 of the light converting member 130. The first and second surfaces 131 and 133 are planar surfaces having the same area and substantially orthogonal to the central axis C. The peripheral surface 135 is disposed between the first and second surfaces 131 and 133.

The light converting member 130 converts at least part of the primary light transmitted through the first reflection member 120 into secondary light. The configuration of the light converting member 130 associated with this conversion will be described below.

The light converting member 130 includes a plurality of body members (not shown) and a first containing member (not shown) containing the body members. The body members are dispersed inside the first containing member and sealed by the first containing member.

The body members include a wavelength converting member (not shown) and a first diffusing member (not shown). Note that the body member may include only the wavelength converting member.

The wavelength converting member absorbs at least part of the primary light with which the wavelength converting member is irradiated and converts the wavelength of the absorbed primary light into a wavelength that is longer than that of the primary light to convert the primary light into secondary light that is wavelength-converted light having a wavelength range that differs from that of the primary light. The wavelength converting member is, for example, powdery fluorescent substances represented by YAG:Ce. The fluorescent substances may be single crystal or polycrystalline. This wavelength converting member absorbs primary light that is light in the blue wavelength range and emits fluorescence in the yellow wavelength range as wavelength-converted light (secondary light). The center wavelength of the fluorescence is, for example, 550 nm. The center wavelength of the fluorescence need not be limited to the numerical value. The fluorescence is emitted isotropically and travels toward the periphery of the light converting member 130. That is, fluorescence travels not only in the forward direction but also in directions other than the forward direction (e.g. lateral and backward directions). Thus, the wavelength converting member can be referred to as a diffusing member in a broad sense.

When the main body members include a wavelength converting member and a first diffusing member, the wavelength converting member acts on the first diffused light having the same wavelength as that of the primary light in the same manner as the primary light.

The first diffusing member converts at least part of the primary light with which the first diffusing member is irradiated, into secondary light that is first diffused light with low coherence, by increasing the spread angle of the primary light and diffusing the primary light, without changing the wavelength of the primary light. In other words, the first diffusing member is a light distribution angle converting member configured to emit light with a light distribution angle that differs from that of the primary light. When the main body members include a wavelength converting member and a first diffusing member, the first diffusing member may convert at least part of the wavelength-converted light (fluorescence, secondary light) into secondary light that is first diffused light with low coherence, by increasing the spread angle of the wavelength-converted light (fluorescence, secondary light) and diffusing the wavelength-converted light (fluorescence, secondary light), without changing the wavelength of the wavelength-converted light (fluorescence, secondary light). As described, the first diffusing member converts at least part of the light with which the first diffusing member is irradiated, into secondary light that is first diffused light with low coherence, by increasing the spread angle of the light and diffusing the light, without changing the wavelength of the light. The light with which the first diffusing member is irradiated includes, for example, the primary light and wavelength-converted light (fluorescence, secondary light). Therefore, the wavelength of the secondary light as the first diffused light generated by the first diffusing member is the same as that of the primary light when the light with which the first diffusing member is irradiated is the primary light, and it is the same as that of the wavelength-converted light (fluorescence, secondary light) when the light with which the first diffusing member is irradiated is the wavelength-converted light (fluorescence, secondary light).

Note that the light converting member 130 converts at least part of the return light with which the light converting member 130 is irradiated and that has the same wavelength as that of the primary light into secondary light. For example, the wavelength converting member and the first diffuse member also act on the second diffused light (tertiary light) that is the return light. The wavelength of the secondary light as the first diffused light generated by the first diffusing member is the same as that of the tertiary light when the light with which the first diffusing member is irradiated is the tertiary light.

The travel of the first diffused light emitted from the first diffusing member will be described with reference to the following general diffusion phenomenon (see Mie scattering and Rayleigh scattering) in the first diffusing member.

The first diffusing member is, for example, fine particles formed of metal or a metal compound. The first diffusing member is alumina, titanium oxide, barium sulfate, or the like. The particle diameter of the first diffusing member is several hundreds of nanometers (nm) to several tens of micrometers (μm). The refractive index of the first diffusing member differs from that of the first containing member. For example, the refractive index of the first diffusing member is preferably higher than that of the first containing member. The first diffusing member thus improves light diffusivity.

The first containing member is formed of a member through which primary light, secondary light, and tertiary light are transmitted. The first containing member is a transparent silicone resin, a transparent epoxy resin, or the like. The first containing member has a high transmittance for the primary light and the secondary light. The first containing member is used to seal the contained member. The first containing member may be glass to seal the first diffusing member that is alumina.

The holding unit 140 of the present embodiment functions as a single first holder 141. The holding unit 140 is shaped like a column, such as a cylinder. The holding unit 140 is a member through which none of the primary light, secondary light, and tertiary light is transmitted. This member may reflect primary light, secondary light, and tertiary light. The member is preferably nickel, brass, SUS, and the like. However, the member need not be limited to these.

The holding unit 140 holds the first reflection member 120 and the light converting member 130 so that the light converting member 130 is separated from the first reflection member 120 and so that the primary light transmitted through the first reflection member 120 enters the light converting member 130. The holding unit 140 controls the relative distance between the first reflection member 120 and the light converting member 130 in the direction of the central axis C of the primary light that travels from the first reflection member 120 to the light converting member 130. In order to control the relative distance, the holding unit 140 includes an orthogonal holding section 151 and a parallel holding section 153.

The holding unit 140 includes a holder entrance portion 161 through which the primary light enters and in which the first reflection member 120 is disposed, and a holder exit portion 163 that emits illumination light including the secondary light. The holder entrance portion 161 is disposed rearward and the holder exit portion 163 is disposed forward. The holding unit 140 further includes a first hollow portion 165, a second hollow portion 167, and a third hollow portion 169, which are arranged in order from the rear to the front. The first, second, and third hollow portions 165, 167, and 169 are through holes penetrating the holding unit 140 in the direction of the central axis C. The first and second hollow portions 165 and 167 are continuous with each other in the direction of the central axis C in the interior of the holding unit 140. The second and third hollow portions 167 and 169 are continuous with each other in the direction of the central axis C in the interior of the holding unit 140.

The first and second hollow portions 165 and 167 are shaped like, for example, a cylinder, and the diameter of the first hollow portion 165 is larger than that of the second hollow portion 167. The ferrule 83 is disposed in the first hollow portion 165 and the transmission member 110 is disposed in the second hollow portion 167. The first hollow portion 165 is engageable with the ferrule 83 and the second hollow portion 167 is engageable with the transmission member 110.

The light converting member 130, diffusing member 180, transparent member 190, orthogonal holding section 151, parallel holding section 153, and second reflection member 200 are disposed in the third hollow portion 169. The first reflection member 120 is preferably disposed in a continuous portion between the second and third hollow portions 167 and 169. The first reflection member 120 may be disposed in the third hollow portion 169.

The holding unit 140 holds the ferrule 83 including the exit end portion of the light guide 80, transmission member 110, first reflection member 120, light converting member 130, diffusing member 180, transparent member 190, orthogonal holding section 151, parallel holding section 153, and second reflection member 200. In the holding unit 140 and on the central axis C, the ferrule 83, transmitting member 110, first reflection member 120 (holder entrance portion 161), orthogonal holding section 151, light converting member 130, diffusing member 180, transparent member 190, and holder exit portion 163 are arranged in this order from the back to the front. The transparent member 190 is filled in the third hollow portion 169 and disposed around the light converting member 130 and the diffusing member 180. Most of the transparent member 190 is disposed in front of the diffusing member 180.

The third hollow portion 169 communicates with the holder entrance portion 161 and the holder exit portion 163. The holder entrance portion 161 is a hole, and is provided with the first reflection member 120. In other words, the first reflection member 120 is disposed on the same plane as the holder entrance portion 161. For example, the holder entrance portion 161 is disposed in a continuous portion between the second and third hollow portions 167 and 169. The size of the holder entrance portion 161 is substantially the same as the size of the first and second surfaces 111 and 113 of the transmission member 110 and the size of the first reflection member 120. The holder exit portion 163 is a hole that is formed closer to an exit face 191 of the transparent member 190 in the third hollow portion 169. Therefore, the holder entrance portion 161 is disposed rearward and the holder exit portion 163 is disposed forward.

The third hollow portion 169 is shaped like a truncated cone gradually expanding toward the holder exit portion 163 from the plane on which the first reflection member 120 is disposed in the direction of the central axis C. Thus, the inner diameter of the holding unit 140 in the third hollow portion 169 gradually increases from the back toward the front in the direction of the central axis C, and the inner peripheral surface of the holding unit 140 in the third hollow portion 169 is a tapered surface. The holding unit 140 has a tapered structure, and the holder exit portion 163 is larger than the holder entrance portion 161.

The orthogonal holding section 151 is disposed along a direction substantially orthogonal to the direction of the central axis C, and is disposed between the first reflection member 120 and the light converting member 130 in the direction of the central axis C. Each of the first reflection member 120 and the light converting member 130 has at least an orthogonal plane formed along a direction substantially orthogonal to the direction of the central axis C. The orthogonal plane of the first reflection member 120 is, for example, the plane of a dielectric film of the first reflection member 120. The orthogonal plane of the light converting member 130 is, for example, the first surface 131 of the light converting member 130. The orthogonal holding section 151 holds the orthogonal planes of the first reflection member 120 and the light converting member 130 in order to control the relative distance by the thickness of the orthogonal holding section 151. In order to hold them, for example, the orthogonal holding section 151 is continuously disposed between the orthogonal plane of the first reflection member 120 and that of the light converting member 130 in the direction of the central axis C. The orthogonal holding section 151 is in contact with the orthogonal plane of the first reflection member 120 and that of the light converting member 130. The orthogonal holding section 151 is preferably in close contact with the entire first reflection member 120 and the entire first surface 131 of the light converting member 130. Thus, the orthogonal holding section 151 is sandwiched between the first reflection member 120 and the first surface 131 of the light converting member 130.

The orthogonal holding section 151 includes a transmission member through which the primary light and the secondary light are transmitted. The transmission member may be a member through which the tertiary light is transmitted as return light. This transmission member is preferably glass such as quartz, a transparent silicone resin, or the like. The transmission member is preferably transparent. However, the transmission member need not be limited to these members. For example, the silicone resin may be brought into close contact with a member (e.g. the first reflection member 120, the first surface 131 of the light converting member 130, and the tapered surface of the holding unit 140) with which the silicone resin is in contact, before the silicon resin is cured. The silicone resin may be cured in close contact with the member. The glass includes a portion that is in contact with the first reflection member 120 and a portion that is in contact with the first surface 131 of the light converting member 130, and these portions are smooth. The smooth portions reduce Fresnel reflection intervening between air layers.

The orthogonal holding section 151 is shaped like a column, such as a truncated cone. The orthogonal holding section 151 exists as a member and is filled in a region between the light converting member 130 and the first reflection member 120 in the third hollow portion 169. Therefore, the orthogonal holding section 151 does not include a layer of gas such as air.

The parallel holding section 153 is included in the inner peripheral surface of the holding unit 140. For example, the parallel holding section 153 functions as part of the tapered surface in the third hollow portion 169. The parallel holding section 153 may be included in the inner peripheral surface of the holding unit 140 in the second hollow portion 167.

Each of the first reflection member 120 and the light converting member 130 has at least a parallel surface that is substantially parallel to the direction of the central axis C. The parallel surface of the first reflection member 120 is, for example, the outer peripheral surface of the dielectric film of the first reflection member 120. The parallel surface of the light converting member 130 is, for example, the peripheral surface 135 that is the outer peripheral surface of the light converting member 130. The parallel holding section 153 holds at least part of at least one parallel surface of the first reflection member 120 and the light converting member 130 in order to control the relative distance. In the present embodiment, for example, at least part of the parallel surface of the first reflection member 120 is an outer peripheral edge (corner) of the peripheral surface. The outer peripheral edge is an outer peripheral edge of a surface where the first reflection member 120 is in contact with the orthogonal holding section 151. At least part of the parallel surface of the light converting member 130 is an outer peripheral edge (corner) of the peripheral surface 135. The outer peripheral edge is a portion where the first surface 131 is in contact with the peripheral surface 135.

Each of the transmission member 110 and the diffusing member 180 has at least a parallel surface that is substantially parallel to the direction of the central axis C. The parallel surface of the transmission member 110 is, for example, a peripheral surface 115 that is the outer peripheral surface of the transmission member 110. The parallel surface of the diffusing member 180 is, for example, a peripheral surface 185 that is the outer peripheral surface of the diffusing member 180. The parallel holding section 153 may hold at least part of each of the parallel surface of the transmission member 110 and the parallel surface of the diffusing member 180 in order to position the transmission member 110 and the diffusing member 180. For example, at least part of the parallel surface of the transmission member 110 corresponds to the entire peripheral surface 110. For example, at least part of the parallel surface of the diffusing member 180 corresponds to an outer peripheral edge (corner) of the peripheral surface 185. Note that the outer peripheral edge is a portion where the first surface 181 is in contact with the peripheral surface 185.

For example, the parallel holding section 153 may hold the parallel surface of the first reflection member 120 over the entire circumference or may hold part of the parallel surface in the circumferential direction. For example, the holding includes at least one of contact, engagement, catch, and adhesion with respect to at least part of the parallel surface. Although the description has been made using the parallel surface of the first reflection member 120, the same holds true for the parallel surface of each of the transmission member 110, light converting member 130, and diffusing member 180.

The position in which the first reflection member 120 and the light converting member 130 are arranged in the direction of the central axis C is controlled based on the relative distance. Accordingly, the position of the parallel holding section 153 in the direction of the central axis C to hold the first reflection member 120 and the light converting member 130 is based on the relative distance. In order to facilitate the positioning of the parallel holding section 153, at least part of the entire tapered surface of the holding unit 140 has only to function as the parallel holding section 153.

The diffusing member 180 is shaped like a column, such as a cylinder. The diffusing member 180 includes a first surface 181 of the diffusing member 180 that is opposed to the second surface 133 of the light converting member 130 and is wider than the second surface 133 of the light converting member 130, a second surface 183 that is a surface opposed to the first surface 181, and a peripheral surface 185 of the diffusing member 180. The first and second surfaces 181 and 183 are planar surfaces that have the same area and that are orthogonal to the central axis C and substantially orthogonal to the central axis C. The peripheral surface 185 is located between the first and second surfaces 181 and 183. The first surface 181 is located on the second surface 133 of the light converting member 130. For example, the first surface 181 is placed on the second surface 133. Thus, the diffusing member 180 is disposed in front of the light converting member 130 and is disposed on the side opposed to the first reflection member 120 with respect to the light converting member 130. The diffusing member 180 is disposed between the light converting member 130 and the holder exit portion 163. At least part of the diffusing member 180 has only to be disposed on the central axis C.

The diffusing member 180 converts at least part of the light with which the diffusing member 180 is irradiated, into second diffused light (tertiary light) with low coherence, by increasing the spread angle of the light and diffusing the light, without changing the wavelength of the light. In other words, the diffusing member 180 is a light distribution angle converting member that emits light with a light distribution angle that differs from that of the light with which the diffusing member 180 is irradiated. The light with which the diffusing member 180 is irradiated includes, for example, the primary light, wavelength-converted light (secondary light), and first diffused light (secondary light). The wavelength of the tertiary light as the second diffused light generated by the diffusing member 180 is the same as that of the primary light when the light with which the diffusing member 180 is irradiated is the primary light, and it is the same as that of the wavelength-converted light (secondary light) when the light with which the diffusing member 180 is irradiated is the wavelength-converted light (secondary light), and it is the same as that of the first diffused light (secondary light) when the light with which the diffusing member 180 is irradiated is the first diffused light (secondary light). The extent of diffusion of the diffusing member 180 may be substantially the same as or different from that of diffusion of the first diffusing member of the light converting member 130.

The travel of the second diffused light emitted from the diffusing member 180 is a general diffusion phenomenon (see Mie scattering and Rayleigh scattering) in the first diffusing member of the light converting member 130, and will be described later.

The diffusing member 180 includes a plurality of second diffusing members (not shown) and a second containing member (not shown) containing the second diffusing members. The second diffusing members are dispersed inside the second containing member and sealed by the second containing member.

The second diffusing member is, for example, fine particles formed of metal or a metal compound. The second diffusing member is alumina, titanium oxide, barium sulfate, or the like. The particle diameter of the second diffusing member is several hundreds of nanometers (nm) to several tens of micrometers (μm). The refractive index of the second diffusing member differs from that of the second containing member. For example, the refractive index of the second diffusing member is preferably higher than that of the second containing member. The second diffusing member thus improves light diffusivity.

The second containing member is formed of a member through which primary light, secondary light, and tertiary light are transmitted. The second containing member is a transparent silicone resin, a transparent epoxy resin, or the like. The second containing member has a high transmittance for the primary light, secondary light, and tertiary light. The second containing member is used to seal the contained member. The second containing member may be glass to seal the second diffusing member that is alumina.

The transparent member 190 is a member through which the primary light, secondary light, and tertiary light is transmitted. This member is preferably glass such as quartz, transparent silicon resin, and the like. The member is preferably transparent. However, the member need not be limited to these elements. The transparent member 190 is shaped like substantially a truncated cone. The entire outer peripheral surface of the transparent member 190 is in contact with the tapered surface of the holding unit 140 with the second reflection member 200 therebetween. The transparent member 190 is in contact with the peripheral surface 135 of the light converting member 130, the second surface 183, the peripheral surface 185, and part of the first surface 181 of the diffusing member 180. The part of the first surface 181 indicates a region where the second surface 133 of the light converting member 130 is not disposed. The exit face 191 of the transparent member 190 is disposed in the holder exit portion 163, and is larger than the first and second surfaces 131 and 133 of the first reflection member 120 and the light converting member 130 and the first and second surfaces 181 and 183 of the diffusing member 180. The exit face 191 emits illumination light forward.

The second reflection member 200 is disposed on an inner peripheral surface that is a tapered surface of the holding unit 140 in the third hollow portion 169. The second reflection member 200 may be disposed on at least a part of the inner peripheral surface. Since the tapered surface of the holding unit 140 includes the parallel holding section 153, the second reflection member 200 is disposed on the parallel holding section 153 in the holder exit portion 163 from the holder entrance portion 163. The second reflection member 200 may be disposed on at least a part of the parallel holding section 153. The parallel holding section 153 holds the first reflection member 120, light converting member 130, and diffusing member 180 through the second reflection member 200.

The second reflection member 200 is also disposed between the first reflection member 120 and the light converting member 130 alongside the orthogonal holding section 151 and in the direction of the central axis C. The second reflection member 200 may be disposed on at least a part of the tapered surface of the holding unit 140 between the first reflection member 120 and the light converting member 130 in the direction of the central axis C.

The second reflection member 200 reflects the light with which the second reflection member 200 is irradiated, toward the holder exit portion 163. The light with which the second reflection member 200 is irradiated includes, for example, primary light, secondary light, and tertiary light.

The second reflection member 200 reflects forward traveling light toward the holder exit portion 163. The second reflection member 200 reflects the return light that returns from the front (closer to the holder exit portion 163) to the back (closer to the holder entrance portion 161), toward the holder exit portion 163. For example, the second reflection member 200 reflects the primary light, secondary light (wavelength-converted light, first diffused light), and tertiary light toward the holder exit portion 163 as return light that returns from the light converting member 130 toward the first reflection member 120.

The second reflection member 200 preferably has a high reflectance for the primary light, secondary light, and tertiary light. When the primary light, secondary light, and tertiary light enter the second reflection member 200, the second reflection member 200 reflects the primary light, secondary light, and tertiary light in specular direction or diffuse direction.

The second reflection member 200 in the present embodiment is, for example, a metal reflection coating (reflecting mirror) whose tapered surface is thinly plated with metal such as silver and aluminum. The second reflection member 200 may be protected by a protective film (not shown). The protective film covers the second reflection member 200. The protective film is a member having a high transmittance, such as a metal oxide film such as silicon dioxide and conductive glass.

The second reflection member 200 is fixed to the tapered surface by an adhesive (not shown) such as resin having a high transmittance. The adhesive is, for example, an epoxy adhesive or a silicone adhesive. The adhesive may be used for bonding between the outer peripheral surface of the ferrule 83 and the inner peripheral surface of the holding unit 140 in the first hollow portion 165, for bonding between the first surface 111 of the transmission member 110 and the distal end face of the ferrule 81 including the exit end face 81, and for bonding between the peripheral surface 115 of the transmission member 110 and the inner peripheral surface of the holding unit 140 in the second hollow portion 167.

In the present embodiment, only the transmission member 110 is disposed between the exit end face 81 and the first reflection member 120, but the disposition of the transmission member 110 need not be limited to this. The illumination unit 100 may include a converging section (not shown) that is disposed between the exit end face 81 and the first reflection member 120 and that is configured to cause the primary light emitted from the exit end face 81 to converge upon the first reflection member 120. The converging section includes, for example, a collimator lens. The converging section adjusts, as desired, the focal length of the primary light and the diameter of a beam spot of the primary light to irradiate the first reflection member 120.

Assume in the present embodiment that, for example, the ferrule 83 is attached to the holding unit 140 so that the exit direction of the primary light emitted from the exit end face 81 is substantially orthogonal to the central axis (vertical direction in FIG. 2) of the holding unit 140. In this case, the illumination unit 100 is disposed between the exit end face 81 and the first reflection member 120, and includes a changing member (not shown) configured to change the travel direction of the primary light toward the first reflection member 120. The changing member includes, for example, a one-plane reflecting prism.

The illumination unit 100 may include a changing member (not shown) configured to change the travel direction of illumination light. The changing member includes, for example, a one-plane reflecting prism. The changing member is attached to, for example, the holder exit portion 163.

The illumination unit 100 may include a third diffusing member (not shown) configured to diffuse illumination light. The third diffusing member is attached to, for example, the holder exit portion 163. The diffusion here includes, for example, refraction, diffraction, and scattering, and the travel direction of the diffused light is changed to two or more directions by the diffusion. Thus, the illumination range of illumination light emitted to the outside expands. The third diffusing member has only to be disposed in front of the holder exit portion 163. Note that not only the third diffusing member but also other optical elements or optical members such as a fluorescent member and a converging member may be disposed. The converging member includes, for example, a collimator lens. The converging member adjusts the diameter of the illumination light as desired.

Next, an example of a procedure for manufacturing the illumination unit 100 will be described with reference to the following Steps 1 to 5.

Step 1: The transmission member 110 is disposed in the second hollow portion 167 with the first reflection member 120 formed on the second surface 113 of the transmission member 110. At this time, the first reflection member 120 is disposed in the holder entrance portion 161.

Step 2: The orthogonal holding section 151 is disposed alongside the first reflection member 120.

Step 3: The light converting member 130 is placed on the orthogonal holding section 151. The outer peripheral edge of the first surface 131 of the light converting member 130 is held by the parallel holding section 153. Mounting and holding are performed simultaneously. Thus, the light converting member 130 is positioned with respect to the first reflection member 120. The relative distance between the first reflection member 120 and the light converting member 130 is controlled as described below. The transparent member 190 is disposed alongside the light converting member 130 in the third hollow portion 169. The transparent member 190 is in contact with the tapered surface and the peripheral surface 135. Then, the transparent member 190 is cured.

Step 4: The diffusing member 180 is placed on the light converting member 130. The transparent member 190 is disposed alongside the diffusing member 180 and between the diffusing member 180 and the holder exit portion 163 in the third hollow portion 169. The transparent member 190 is filled in the third hollow portion 169. Then, the transparent member 190 is cured.

Step 5: An adhesive (not shown) is applied to at least one of the outer peripheral surface of the ferrule 83 and the inner peripheral surface of the holder in the first hollow portion 165. The ferrule 83 with which the light guide 80 is engaged is inserted into the first hollow portion 165 so that the exit end face 81 is optically connected to the transmission member 110. When the adhesive is cured, the outer peripheral surface of the ferrule 83 is bonded to the inner peripheral surface of the holder in the first hollow portion 165.

Step 5 may be executed before Step 1.

Next, specific control of the relative distance will be described.

Figure 3A:
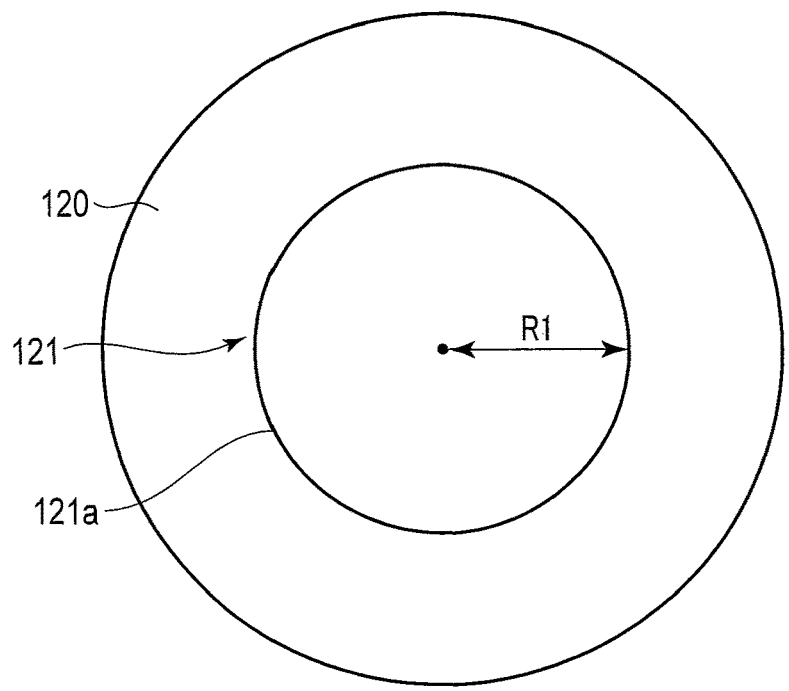
FIG. 3A is a diagram illustrating example 1 of an index value.
Figure 3B:
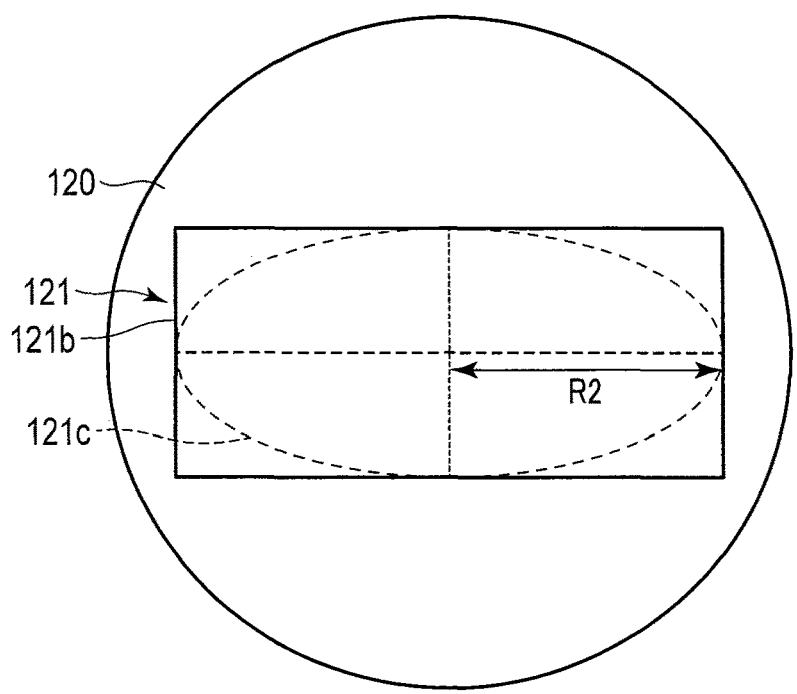
FIG. 3B is a diagram illustrating example 2 of the index value.

The holding unit 140 controls the relative distance on the basis of secondary light transmittance and an index value indicating the size of a first irradiation area 121 shown in FIGS. 3A and 3B. The first irradiation area 121 is an area of the first reflection member 120 that is irradiated with secondary light (e.g. wavelength-converted light) that returns from the light converting member 130 to the first reflection member 120. The secondary light transmittance is the transmittance of the first reflection member 120 for the second wavelength of the secondary light (e.g. wavelength-converted light).

First, the index value will be described.

The first irradiation area 121 shown in FIGS. 3A and 3B is formed in a plane located along a direction that is substantially orthogonal to the direction of the central axis C. This plane is opposed to the first surface 131 of the light converting member 130. The first irradiation area 121 is planar and has a two-dimensional shape projected onto a plane that is substantially orthogonal to the central axis C.

As example 1 of the index value, when the planar shape of the first irradiation area 121 is an approximate circle 121a as shown in FIG. 3A, the index value uses the radius R1 of the approximate circle 121a as an effective radius.

Next, example 2 of the index value will be described. In example 2, the planar shape of the first irradiation area 121 is a plane other than the approximate circle 121a.

As example 2 of the index value, when the planar shape of the first irradiation area 121 is, for example, an approximate rectangle 121b as shown in FIG. 3B, the index value uses the major axis radius R2 of an approximate ellipse 121c inscribed on the approximate rectangle 121b as an effective radius. The major axis radius R2 is the greatest width of the first irradiation area 121 that passes through the center of the first irradiation area 121.

Although not shown, as example 3 of the index value, when the planar shape of the first irradiation area 121 is, for example, an approximate ellipse, the index value uses the major axis radius of the approximate ellipse as an effective radius.

Hereinafter, the radius R1 or the major axis radius R2 that is the index value will be defined as an index radius R3.

Figure 3C:
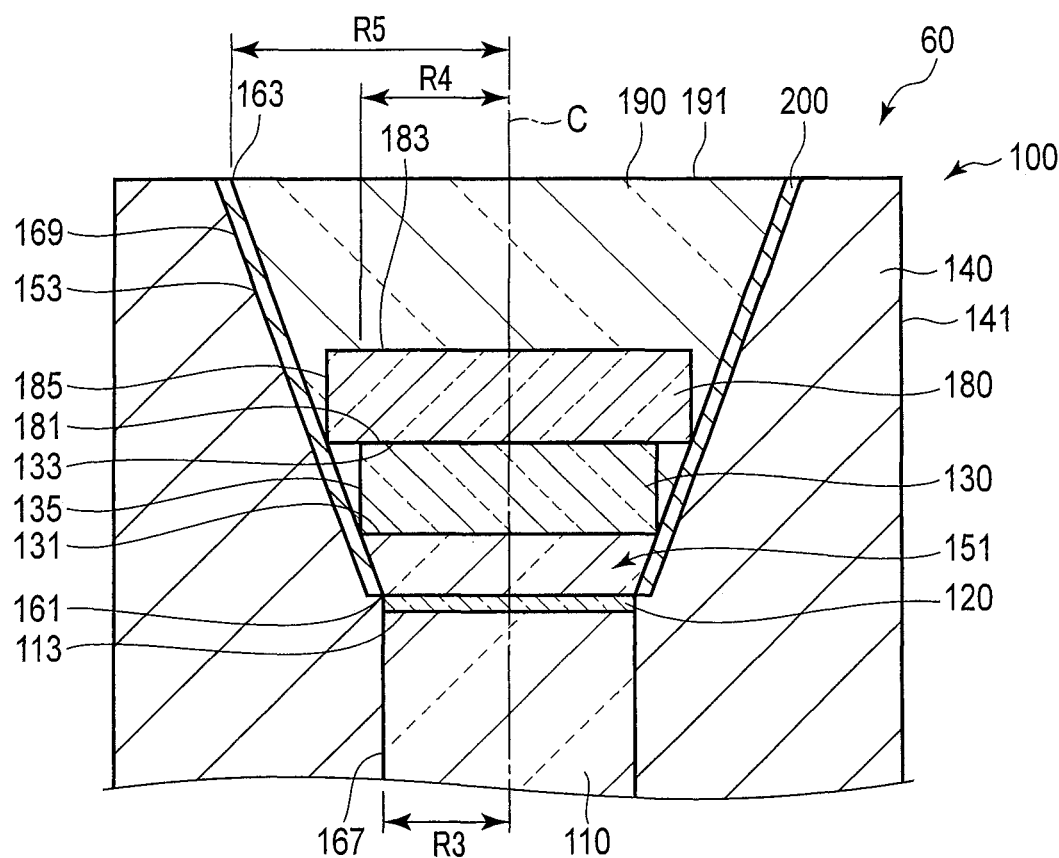
FIG. 3C is a diagram illustrating the upper limit of a relative distance.

Next, the upper limit value (maximum length) of the relative distance will be described with reference to FIG. 3C.

Here, the radius of the first surface 131 of the light converting member 130 irradiated with the primary light emitted from the first reflection member 120 is defined as a radius R4. The first surface 131 emits return light (e.g. secondary light (wavelength-converted light and first diffused light) and tertiary light (second diffused light)). The radius of the holder exit portion 163 will be defined as a radius R5. The upper limit value of the relative distance satisfies the following expressions (1) and (2).

$$R3 < R4 \qquad \text{Expression (1):}$$

$$R4 < R5 \qquad \text{Expression (2):}$$

With the upper limit value of the relative distance that satisfies the expressions (1) and (2), the tapered structure is also maintained and the illumination light is efficiently emitted forward in the holding unit 140. Note that if the illumination light is efficiently emitted forward, the holding unit 140 may have a structure (e.g. parabolic shape) other than the tapered structure. Thus, the radius R4 of the first surface 131 may be substantially the same as the radius R5 of the holder exit portion 163. That is, the expression (3) is obtained in consideration of the expression (2).

$$R4 \leq R5 \qquad \text{Expression (3):}$$

As described above, the holding unit 140 controls the relative distance so that the index value is less than the radius of the first surface 131 of the light converting member 130 and so that the radius of the first surface 131 is less than the radius of the holder exit portion 163 or substantially equal to the radius of the holder exit portion 163.

Note that the radius of the holder entrance portion 161 (the radius of the first reflection member 120) is less than the radius R4.

Next, the secondary light transmittance will be described with reference to FIGS. 3D and 3E.

The light converting member 130 includes a second irradiation area 137 irradiated with primary light that travels from the first reflection member 120 to the light converting member 130. The second irradiation area 137 is formed in a plane located along a direction that is substantially orthogonal to the direction of the central axis C. This plane is located on the first surface 131 of the light converting member 130. The second irradiation area 137 is a plane and has a two-dimensional shape projected onto a plane that is substantially orthogonal to the central axis C. The second irradiation area 137 may be the entire first surface 131 or may be smaller than the first surface 131.

The primary light emitted from the exit end face 81 is most strongly applied onto the central axis C. The position in the light converting member 130 to which the primary light is applied most strongly is a position where the central axis C and the first surface 131 (second irradiation area 137) of the light converting member 130 irradiated with the primary light intersect, and is also a position where part of the primary light is absorbed and the intensity of the wavelength-converted light (secondary light) becomes the strongest. The intersection of the second irradiation area 137 and the central axis C will be defined as a substantial light emitting point P of the light converting member 130. The wavelength-converted light (secondary light) is generated from an area including the substantial light emitting point P and is isotropically emitted. Thus, part of the wavelength-converted light (secondary light) returns (travels) as return light from the area including the light emitting point P toward the first reflection member 120. Pay attention here to the secondary light (e.g. wavelength-converted light) as return light from the light converting member 130 to the first reflection member 120.

Here, the incident angle of the secondary light (e.g. wavelength-converted light) as return light to the first reflection member 120 is defined as incident angle α. The incident angle α is a desired value. The incident angle α can be regarded as, for example, an angle formed by the intersection of the central axis C2 of the secondary light (e.g. wavelength-converted light) as return light emitted from the light emitting point P toward the first reflection member 120 and the secondary light (e.g. wavelength-converted light) that returns to the peripheral edge 121e of the first irradiation area 121.

Here is a description of the transmission and reflection of the first reflection member 120 with respect to, for example, the secondary light (e.g. wavelength-converted light) as return light whose center wavelength is nearly 680 nm.

Figure 3E:
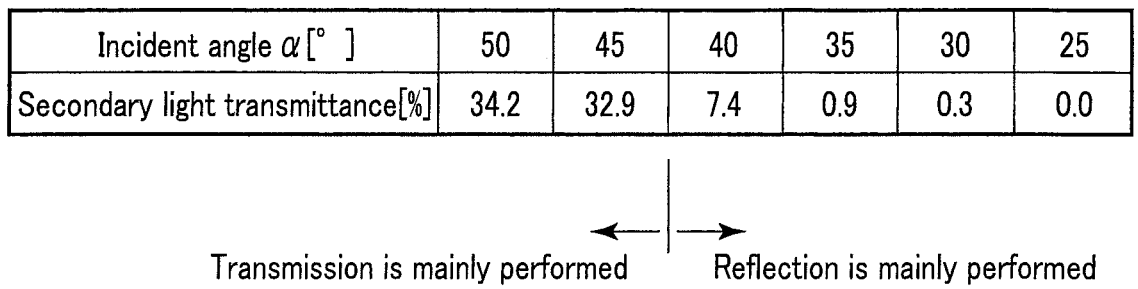
FIG. 3E is a table illustrating a relationship between the incident angle and secondary light transmittance.

As shown in FIG. 3E, for example, the applicant has confirmed that when the incident angle α with respect to the dielectric film of the first reflection member 120 is 45° or more, the secondary light transmittance increases and the second reflectance decreases, and when the incident angle α is less than 45°, the secondary light transmittance decreases and the second reflectance increases. As a result of the confirmation, for example, when the incident angle α is 50°, 45°, 40°, 35°, 30°, and 25°, their respective secondary light transmittances are 34.2%, 32.9%, 7.4%, 0.9%, 0.3%, and 0.0%. It is confirmed that the transmission is mainly performed when the incident angle α is 45° or more, and the reflection is mainly performed when the incident angle α is less than 45°. It is confirmed that the reflectance of the secondary light (e.g. wavelength-converted light) increases when the incident angle α is less than 45°.

For example, when the incident angle α is 45° or more, the secondary light transmittance is high and the secondary reflectance is low, and part of the secondary light (e.g. wavelength-converted light) as return light is transmitted through the first reflection member 120 and returns (travels) toward the light source unit 70 through the light guide 80. Therefore, the return light is not used as illumination light or illumination light is not emitted with efficiency, with the result that a desired quantity of light is not obtained.

When the incident angle α is, for example, less than 45°, the secondary light transmittance is low and the secondary reflectance is high, and most of the secondary light (e.g. wavelength-converted light) as return light is reflected forward by the first reflection member 120, the return of the secondary light (e.g. wavelength-converted light) to the light source unit 70 is reduced, and the secondary light (e.g. wavelength-converted light) reflected forward is used as illumination light. Thus, illumination light is emitted with efficiency and a desired quantity of light is obtained. That is, the secondary light transmittance needs to decrease (the second reflectance needs to increase), and the incident angle α needs to be less than 45°.

It is preferable that in consideration of the confirmation result, the transmittance of the first reflection member 120 for the primary light, the secondary light transmittance, and the first and second reflectances, the incident angle α have an angle at which the secondary light transmittance is, for example, 30% or more. It is more preferable that the incident angle α have an angle at which the secondary light transmittance is, for example, 30% or more and less than 32.9%. The physical properties of the first reflection member 120 vary with the material, film thickness and film number of the first reflection member 120, the wavelength of the secondary light (e.g. wavelength-converted light), and the like. It is thus preferable that the incident angle α be set to an angle suitable for the transmittance characteristics of the first reflection member 120.

In order to irradiate the first reflection member 120 with the secondary light whose incident angle α is less than 45° (e.g. wavelength-converted light) as return light, the relative distance is preferably maintained at a value obtained by the index radius R3, the incident angle α and the trigonometric function.

When the relative distance is D as shown in FIG. 3D, the holding unit 140 controls the relative distance D so that the relative distance D is equal to or greater than the value obtained by dividing the index radius R3 by a tangent (tan α). The relative distance D is thus obtained by the following expression (4).

$$D \geq R3/\tan \alpha \qquad \text{Equation (4):}$$

Assume here that the incident angle α is 45°. The following expression (5) is thus obtained based upon the expression (4).

$$D \geq R3 \qquad \text{Equation (5):}$$

Therefore, the illumination unit 100 preferably has a relative distance D that is equal to or greater than the index radius R3.

When the relative distance D is equal to or greater than the index radius R3, the secondary light (e.g. wavelength-converted light) as return light whose incident angle is 45° or more with respect to the first reflection member 120, is decreased. Accordingly, the transmission of the secondary light (e.g. wavelength-converted light) for the first reflection member 120 and the transmission member 110 is reduced, and the return of the secondary light (e.g. wavelength-converted light) to the light source unit 70 is reduced. When the relative distance D is equal to or greater than the index radius R3, the secondary light (e.g. wavelength-converted light) as return light whose incident angle is less than 45° with respect to the first reflection member 120, is increased. Accordingly, the secondary light (e.g. wavelength-converted light) as return light to the first reflection member 120 is increased. Most of the secondary light (e.g. wavelength-converted light) as return light from the front to the first reflection member 120 is reflected forward (light converting member 130) by the first reflection member 120, and is used as illumination light. The illumination light is thus emitted with efficiency and a desired quantity of light is obtained.

In order to prevent the secondary light (e.g. wavelength-converted light) whose index radius R3 is 100 μm and whose incident angle α is 120° or more with respect to the first reflection member 45 from being transmitted, at least 100 μm is required as the relative distance D as is seen from the expression (5).

The relative distance is controlled in advance based on the expression (5) in accordance with, e.g. a use of the illumination unit 100, for example, before the illumination unit 100 is produced.

Next, an example of an operation in which illumination light is generated by the illumination unit 100 and emitted from the illumination unit 100 to the front of the illumination unit 100, will be described with reference to FIGS. 4A and 4B.

Although not shown, primary light is emitted from the light source unit 70 and guided by the light guide 80. As shown in FIG. 4A, the primary light is emitted from the exit end face 81 toward the illumination unit 100. The light distribution of the primary light emitted from the exit end face 81 is narrow, and the light distribution half-value angle is, for example, approximately 15°. The intensity of the primary light is highest on the central axis C.

As shown in FIG. 4A, the primary light that has reached the illumination unit 100 is transmitted through the transmission member 110 and reaches the first reflection member 120. Most of the primary light is transmitted through the first reflection member 120. Although not shown, the remainder of the primary light is reflected by the first reflection member 120 and returns to the light source unit 70 through the light guide 80. The quantity of primary light returned to the light source unit 70 is much smaller than the quantity of primary light transmitted through the first reflection member 120 due to the first reflectance of the first reflection member 120.

As shown in FIG. 4A, the primary light transmitted through the first reflection member 120 passes through the orthogonal holding section 151 and enters the light converting member 130. Assume here that part of the primary light that has entered the light converting member 130 is not absorbed by the wavelength converting member, but passes through the light converting member 130 without irradiating the first diffusing member, other part thereof is absorbed by the wavelength converting member, and other part thereof irradiates with the first diffusing member.

Here is a description of the primary light that is not absorbed by the wavelength converting member but transmitted through the light converting member 130 without irradiating the first diffusing member.

As shown in FIG. 4A, part of the primary light transmitted through the light converting member 130 enters the diffusing member 180, and its spread angle is increased and it is diffused and emitted as second diffused light (tertiary light) by the diffusing member 180, without changing the wavelength of the primary light. The wavelength of the second diffused light (tertiary light) is the same as that of the primary light. Part of the second diffused light (tertiary light) emitted from the diffusing member 180 travels forward to irradiate the second reflection member 200. The second diffused light (tertiary light) is reflected forward by the second reflection member 200 and its travel direction changes. Then, the second diffused light (tertiary light) is emitted from the holder exit portion 163 as illumination light, without re-entering the light converting member 130 and the diffusing member 180. The light distribution of the second diffused light (tertiary light) is converted by the second reflection member 200, and the components thereof traveling forward from the periphery are increased. Thus, a light distribution whose angle is narrower than that of an isotropic light distribution is achieved. Although not shown, the remaining part of the second diffused light (tertiary light) emitted forward does not travel to the second reflection member 200, but is transmitted through the transparent member 190 and emitted directly from the holder exit portion 163 as illumination light. That is, the travel direction of the second diffused light (tertiary light) is not changed by the second reflection member 200, but the remaining part of the second diffused light (tertiary light) is emitted as illumination light.

Although not shown, a remaining part of the primary light transmitted through the light converting member 130 does not travel to the second reflection member 200, but is transmitted through the diffusing member 180 and the transparent member 190 and emitted directly from the holder exit portion 163 as illumination light. That is, part of the primary light is emitted without changing the travel direction of the primary light by the second reflection member 200. Although not shown, a further remaining part of the primary light transmitted through the light converting member 130 may pass through the diffusing member 180 and the transparent member 190 and irradiate the second reflection member 200. The primary light is reflected forward by the second reflection member 200 and its travel direction changes. The primary light does not travel backward but is emitted from the holder exit portion 163 as illumination light without re-entering the diffusing member 180 and the light converting member 130. The light distribution of the primary light is converted by the second reflection member 200, and the components thereof traveling forward from the periphery are increased. Thus, a light distribution whose angle is narrower than that of an isotropic light distribution is achieved.

The illumination light is thus emitted with efficiency, and a desired quantity of light is obtained.

Next is a description of the primary light absorbed by the wavelength converting member of the light converting member 130.

The primary light absorbed by the wavelength converting member is wavelength-converted into wavelength-converted light (secondary light that is yellow fluorescent light), and isotropically emitted from the substantial light emitting point P of the light converting member 130, and travels toward the periphery of the light converting member 130.

Here is a description of the wavelength-converted light (secondary light) that travels toward the front of the light converting member 130. The same applies to the wavelength-converted light (secondary light) that travels toward the side of the light converting member 130. The wavelength-converted light (secondary light) travels to at least one of the front and the side thereof.

As shown in FIG. 4A, part of the wavelength-converted light (secondary light) that travels toward the front of the light converting member 130 is transmitted through the diffusing member 180 and the transparent member 190 to irradiate the second reflection member 200. The wavelength-converted light (secondary light) is reflected forward by the second reflection member 200 and its travel direction changes. Then, the wavelength-converted light (secondary light) does not travel backward but is emitted as illumination light from the holder exit portion 163 without re-entering the diffusing member 180 and the light converting member 130. The light distribution of the wavelength-converted light (secondary light) is converted by the second reflection member 200, and the components thereof traveling forward from the periphery are increased. Thus, a light distribution whose angle is narrower than that of an isotropic light distribution is achieved. Although not shown, the remaining part of the wavelength-converted light (secondary light) emitted forward from the light converting member 130 does not travel to the second reflection member 200, but is transmitted through the diffusing member 180 and the transparent member 190 and emitted directly from the holder exit portion 163 as illumination light. That is, the travel direction of the wavelength-converted light (secondary light) is not changed by the second reflection member 200, but the remaining part of the wavelength-converted light (secondary light) is emitted as illumination light.

Although not shown, a further remaining part of the wavelength-converted light (secondary light) enters the diffusing member 180, and its spread angle is increased and it is diffused and emitted as second diffused light (tertiary light) by the diffusing member 180, without changing the wavelength of the wavelength-converted light (secondary light). The wavelength of the second diffused light (tertiary light) is the same as that of the wavelength-converted light (secondary light). Although not show, part of the second diffused light (tertiary light) emitted from the diffusing member 180 travels forward to irradiate the second reflection member 200. The second diffused light (tertiary light) is reflected forward by the second reflection member 200 and its travel direction changes. Then, the second diffused light (tertiary light) does not travel backward but is emitted as illumination light from the holder exit portion 163, without re-entering the diffusing member 180 and the light converting member 130. The light distribution of the second diffused light (tertiary light) is converted by the second reflection member 200, and the components thereof traveling forward from the periphery are increased. Thus, a light distribution whose angle is narrower than that of an isotropic light distribution is achieved. Although not shown, the remaining part of the second diffused light (tertiary light) emitted forward from the diffusing member 180 does not travel to the second reflection member 200, but is transmitted through the transparent member 190 and emitted as illumination light directly from the holder exit portion 163. That is, the travel direction of the second diffused light (tertiary light) is not changed by the second reflection member 200, but the remaining part of the second diffused light (tertiary light) is emitted as illumination light.

Illumination light is thus emitted with efficiency, and a desired quantity of light is obtained.

The wavelength-converted light (secondary light) as return light that returns backward from the light converting member 130 will be described below with reference to FIG. 4B.

In a wavelength converting member (not shown) of the light converting member 130, the wavelength-converted light (secondary light) is isotropically emitted from the light converting member 130. Accordingly, for example, part of the wavelength-converted light (secondary light) is emitted backward from the first surface 131 of the light converting member 130 and returned backward from the first surface 131 of the light converting member 130 through the orthogonal holding section 151.

In the present embodiment, the light converting member 130 is separated from the first reflection member 120, and the relative distance is controlled. Thus, part of the wavelength-converted light (secondary light) that returns backward passes through the orthogonal holding section 151 and irradiates the first reflection member 120. In the wavelength-converted light (secondary light) whose incident angle to the first reflection member 120 is large, the separation decreases the wavelength-converted light (secondary light) as return light that returns to the first reflection member 120. Accordingly, the transmission of the wavelength-converted light (secondary light) through the first reflection member 120 and the transmission member 110 is reduced, so that the return of the wavelength-converted light (secondary light) to the light source unit 70 is reduced. The separation also increases the wavelength-converted light (secondary light) whose incident angle with respect to the first reflection member 120 is small and increases the wavelength-converted light (secondary light) as return light that returns to the first reflection member 120. Thus, part of the wavelength-converted light (secondary light) that returns to the first reflection member 120 from the front, such as the side of the light converting member 130, is reflected forward (toward the light converting member 130) by the first reflection member 120. The wavelength-converted light (secondary light) is emitted as illumination light from the holder exit portion 163 through the orthogonal holding section 151 and light converting member 130 and also through the diffusing member 180 and transparent member 190 (neither of which is shown). Although not shown, the wavelength-converted light (secondary light) reflected by the first reflection member 120 may travel to the second reflection member 200, may be reflected forward by the second reflection member 200, and may be emitted as illumination light from the holder exit portion 163. Although not shown, for example, the wavelength-converted light (secondary light) may be diffused without changing its wavelength in the first diffusing member and the diffusing member 180 of the light converting member 130. The travel of the wavelength-converted light (secondary light) to the holder exit portion 163 is substantially the same as described above.

Other part of the wavelength-converted light (secondary light) that returns backward passes through the orthogonal holding section 151 and irradiates the second reflection member 200. The second reflection member 200 in the present embodiment is disposed between the light converting member 130 and the first reflection member 120 alongside the orthogonal holding section 151, namely, in the direction of the central axis C. Thus, the wavelength-converted light (secondary light) is reflected forward by the second reflection member 200 and its travel direction is changed forward. Then, the wavelength-converted light (secondary light) is emitted as illumination light from the holder exit portion 163 through the light converting member 130 and through the diffusing member 180 and the transparent member 190 (neither of which is shown). Although not shown, for example, the wavelength-converted light (secondary light) may be diffused without changing its wavelength in the first diffusing member and the diffusing member 180 of the light converting member 130. The travel of the wavelength-converted light (secondary light) to the holder exit portion 163 is substantially the same as described above. In the third hollow portion 169, the inner diameter of the holding unit 140 is gradually narrowed from the front toward the back in the direction of the central axis C. The second reflection member 200 is also disposed between the first reflection member 120 and the light converting member 130 alongside the orthogonal holding section 151, namely, in the direction of the central axis C. Therefore, the wavelength-converted light (secondary light) reflected by the second reflection member 200 does not travel to the first reflection member 120 but travels only forward and is emitted as illumination light from the holder exit portion 163.

The wavelength-converted light (secondary light) as return light that returns to the second reflection member 200 is light whose incident angle $\alpha$ is 45° or more. Even though the incident angle $\alpha$ of the light is 45° or more, the second reflection member 200 reflects the light forward. In the present embodiment, therefore, the wavelength-converted light (secondary light) as return light is reflected forward by the second reflection member 200 and used as the illumination light, even though the incident angle $\alpha$ of the light is 45° or more.

As described above, the return light is used as illumination light, the illumination light is emitted with efficiency, and a desired quantity of light is obtained.

Next is a description of the primary light with which the first diffusing member of the light converting member 130 is irradiated.

First, a general diffusion phenomenon in the first diffusing member will be described. The diffusion phenomenon is largely divided into Mie scattering and Rayleigh scattering.

The Mie scattering occurs when the diameter of the first diffusing member is substantially the same as the wavelength of the primary light. In the Mie scattering, there are a large number of forward scattering components indicating components in which the first diffused light (secondary light) is scattered (traveled) in front of the first diffusing member, and there are a small number of backward scattering components indicating components in which the first diffused light (secondary light) is scattered (traveled) behind the first diffusing member.

The Rayleigh scattering occurs when the diameter of the first diffusing member is approximately ⅒ or less of the wavelength of the primary light. In the Rayleigh scattering, the forward scattering components are substantially the same as the backward scattering components.

In view of the brightness of illumination light emitted forward from the holder exit portion 163, it is preferable in the present embodiment to utilize the Mie scattering in which the forward scattering components are larger than the backward scattering components. On the other hand, in order to scatter multicolor primary light, the wavelength dependence of the scattering should be taken into consideration. It is generally considered that the wavelength dependence of the Mie scattering is greater than that of the Rayleigh scattering, and the Rayleigh scattering is preferable in order to eliminate color unevenness of illumination light.

Regardless of which of the Mie scattering and the Rayleigh scattering is used, when the first diffused light (secondary light) is generated, not only forward scattering components but also backward scattering components are generated. The first diffusing member emits part of the first diffused light (secondary light) as illumination light toward the front, but also emits the remaining part of the first diffused light (secondary light) toward the back as return light. In other words, the first diffused light (secondary light) travels to the periphery of the first diffusing member. The forward scattering components are used as illumination light, and the backward scattering components do not contribute to the illumination light.

Under the situation where the above diffusion phenomenon occurs, the primary light irradiates the first diffusing member. The primary light with which the first diffusing member is irradiated is diffused as first diffused light (secondary light) by expanding the spread angle of the primary light without changing the wavelength of the primary light. The wavelength of the first diffused light (secondary light) is the same as that of the primary light.

Referring now to FIG. 4A, the forward scattering components, that is, the first diffused light (secondary light) that travels in front of the light converting member 130 will be described. Here is a description of the first diffused light (secondary light) that travels forward, and the same applies to the first diffused light (secondary light) that travels toward the side of the light converting member 130. The first diffused light (secondary light) travels to at least one of the front and the side.

As shown in FIG. 4A, part of the first diffused light (secondary light) that travels in front of the light converting member 130 passes through the diffusing member 180 and the transparent member 190, and irradiates the second reflection member 200. The first diffused light (secondary light) is reflected forward by the second reflection member 200 and its travel direction is changed. Then, the first diffused light (secondary light) does not travel backward but is emitted from the holder exit portion 163 as illumination light without re-entering the diffusing member 180 and the light converting member 130. The light distribution of the first diffused light (secondary light) is converted by the second reflection member 200, and the components thereof traveling forward from the periphery are increased. Thus, a light distribution whose angle is narrower than that of an isotropic light distribution is achieved. Although not shown, the remaining part of the first diffused light (secondary light) emitted forward from the light converting member 130 does not travel to the second reflection member 200, but is transmitted through the diffusing member 180 and the transparent member 190 and emitted directly from the holder exit portion 163 as illumination light. That is, the travel direction of the first diffused light (secondary light) is not changed by the second reflection member 200, but the remaining part of the first diffused light (secondary light) is emitted as illumination light.

Although not shown, a further remaining part of the first diffused light (secondary light) enters the diffusing member 180, and its spread angle is increased and it is diffused and emitted as second diffused light (tertiary light) by the diffusing member 180, without changing the wavelength of the first diffused light (secondary light). Since the wavelength of the first diffused light (secondary light) is the same as that of the primary light, the wavelength of the second diffused light (tertiary light) is the same as that of the primary light. Although not show, part of the second diffused light (tertiary light) emitted from the diffusing member 180 travels forward to irradiate the second reflection member 200. The second diffused light (tertiary light) is reflected forward by the second reflection member 200 and its travel direction changes. Then, the second diffused light (tertiary light) does not travel backward but is emitted as illumination light from the holder exit portion 163, without re-entering the diffusing member 180 and the light converting member 130. The light distribution of the second diffused light (tertiary light) is converted by the second reflection member 200, and the components thereof traveling forward from the periphery are increased. Thus, a light distribution whose angle is narrower than that of an isotropic light distribution is achieved. Although not shown, the remaining part of the second diffused light (tertiary light) emitted forward from the diffusing member 180 does not travel to the second reflection member 200, but is transmitted through the transparent member 190 and emitted as illumination light directly from the holder exit portion 163. That is, the travel direction of the second diffused light (tertiary light) is not changed by the second reflection member 200, but the remaining part of the second diffused light (tertiary light) is emitted as illumination light.

Here is a description of the diffusion for the primary light. The same is true for the diffusion for the wavelength-converted light (secondary light).

The illumination light is thus emitted with efficiency, and a desired quantity of light is obtained.

Referring now to FIG. 4B, the backward scattering components, that is, the first diffused light (secondary light) that travels behind the light converting member 130 will be described.

According to the present embodiment, in the third hollow portion 169, the inner diameter of the holding unit 140 is gradually narrowed from the front (light converting member 130) toward the back (first reflection member 120) in the direction of the central axis C. The second reflection member 200 is also disposed between the first reflection member 120 and the light converting member 130 alongside the orthogonal holding section 151, namely, in the direction of the central axis C. Thus, most of the first diffused light (secondary light) as return light that returns to the back from the front, travels not to the first reflection member 120 but to the second reflection member 200. The second reflection member 200 reflects the first diffused light (secondary light), which returns backward from the light converting member 130 and irradiates the second reflection member 200, forward so that the first diffused light (secondary light) as return light does not re-enter the light guide 80 but travels to the front, such as toward the light converting member 130. Thus, the first diffused light (secondary light) reflected by the second reflection member 120 does not travel to the first reflection member 120 but travels forward only. The travel of the first diffused light (secondary light) to the holder exit portion 163 is substantially the same as described above, and the first diffused light (secondary light) is emitted as illumination light.

Although not shown, part of the first diffused light (secondary light) as return light that returns backward from the light converting member 130 returns to the first reflection member 120. The wavelength of the first diffused light (secondary light) is the same as that of the primary light. Therefore, although not shown, most of the first diffused light (secondary light) returned to the first reflection member 120 passes through the first reflection member 120 and returns to the light source unit 70. In the present embodiment, however, the quantity of first diffused light (secondary light) that returns to the first reflection member 120 by the tapered structure and the second reflection member 200 is much smaller than the quantity of first diffused light (secondary light) that travels to the second reflection member 200. That is, most of the first diffused light (secondary light)

as return light travels not to the first reflection member 120 but to the second reflection member 200, and is reflected forward by the second reflection member 200 and emitted as illumination light.

As described above, the return light is used as illumination light, the illumination light is emitted with efficiency, and a desired quantity of light is obtained.

Like the general diffusion phenomenon in the first diffusing member, a general diffusion phenomenon in the diffusing member 180 is largely divided into Mie scattering and Rayleigh scattering. Therefore, although not shown, return light is also generated by the diffusing member 180. Although not shown, the return light is reflected forward by the tapered structure and the second reflection member 200 and used as illumination light, as in the first diffusing member described above. Thus, the return light is used as illumination light, the illumination light is emitted with efficiency, and a desired quantity of light is obtained.

In the present embodiment, therefore, regardless of whether the wavelength of the return light is the same as or different from that of the primary light, the return light that returns backward is reflected forward by the tapered structure and the second reflection member 200 and emitted from the holder exit portion 163 as illumination light. When the return light is wavelength-converted light (secondary light), the wavelength-converted light (secondary light) is further reflected forward by the first reflection member 120 and emitted from the holder exit portion 163 as illumination light. When the wavelength of the return light is the same as that of the primary light, most of the return light passes through the first reflection member 120 and returns to the light source unit 70. However, in the present embodiment, the quantity of return light that returns to the first reflection member 120 by the tapered structure and the second reflection member 200 is much smaller than the quantity of return light that returns to the second reflection member 200. That is, most of the return light travels not to the first reflection member 120 but to the second reflection member 200, and is reflected forward by the second reflection member 200 and used as illumination light. Thus, the illumination light is emitted with efficiency and a desired quantity of light is obtained.

As described above, in the present embodiment, the light converting member 130 is separated from the first reflection member 120 by the holding unit 140, and the relative distance is controlled by the holding unit 140. Thus, in the wavelength-converted light (secondary light) whose incident angle with respect to the first reflection member 120 is large, the wavelength-converted light (secondary light) as return light that returns to the first reflection member 120 can be decreased, the transmission of the wavelength-converted light (secondary light) to the first reflection member 120 and the transmission member 110 can be decreased, and the return of the wavelength-converted light (secondary light) to the light source unit 70 can be decreased. Furthermore, the wavelength-converted light whose incident angle with respect to the first reflection member 120 is small can be increased, as can be the wavelength-converted light (secondary light) as return light that returns to the first reflection member 120. Most of the wavelength converted light (secondary light) that returns from the light converting member 130 to the first reflection member 120 can be reflected forward (toward the light converting member 130) by the first reflection member 120 and emitted as illumination light. As described above, in the present embodiment, the wavelength-converted light (secondary light) as return light can be used as illumination light, the illumination light can be emitted with efficiency, and a desired quantity of light can be obtained.

In the present embodiment, since the relative distance is controlled based upon the index value and the secondary light transmittance, the relative distance can easily be controlled, the illumination light can efficiently be emitted, with a result that a desired quantity of light can be obtained.

In the present embodiment, in the third hollow portion 169, the inner diameter of the holding unit 140 gradually increases from the plane on which the first reflection member 120 is located toward the holder exit portion 163. Therefore, when the light converting member 130 is disposed in the third hollow portion 169, the parallel holding section 153 can hold the light converting member 130 reliably and position the light converting member 130 reliably, with the result that the relative distance can reliably be controlled.

In the present embodiment, the orthogonal holding section 151 can position the light converting member 130 reliably and control the relative distance reliably.

In the present embodiment, even though the incidence angle α of the wavelength-converted light (secondary light) as return light that returns to the second reflection member 200 is 45° or more, the light can be reflected forward by the tapered structure and the second reflection member 200. Therefore, in the present embodiment, the wavelength-converted light (secondary light) as return light can be used as illumination light.

In the present embodiment, regardless of whether the wavelength of the return light is the same as or different from that of the primary light, the return light that returns backward can be reflected forward by the tapered structure and the second reflection member 200 and emitted from the holder exit portion 163 as illumination light. When the return light is wavelength-converted light (secondary light), the wavelength-converted light (secondary light) can be further reflected forward by the first reflection member 120 and emitted from the holder exit portion 163 as illumination light. In the present embodiment, therefore, the efficiency with illumination light is extracted from the primary light can be improved, and the primary light can be used as illumination light without waste. Then, bright illumination light can be provided to an observation target.

Modification

Figure 5:
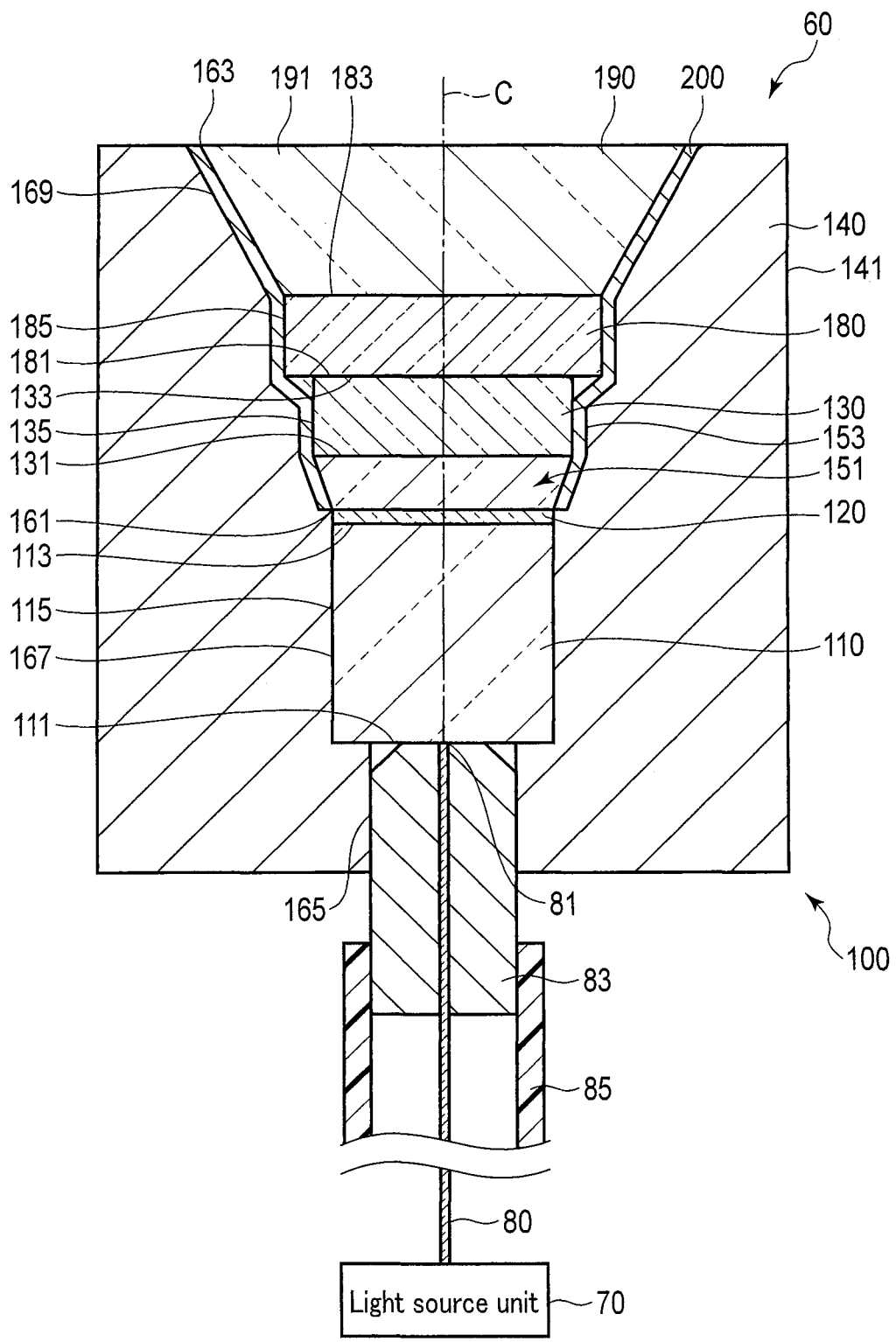
FIG. 5 is a diagram schematically showing an illumination device of a modification to the first embodiment.

A modification to the present embodiment will be described below with reference to FIG. 5. In this modification, only differences from the first embodiment will be described.

The parallel holding section 153 holds almost all the peripheral surface 135 of the light converting member 130 that is a parallel surface of the light converting member 130. The parallel holding section 153 holds the peripheral surface 135 all over the circumference. The parallel holding section 153 may hold the entire peripheral surface 185 of the diffusing member 180 that is a parallel surface of the diffusing member 180.

Thus, a part of the inner peripheral surface of the third hollow portion 169 is a parallel surface that is substantially parallel to the direction of the central axis C.

Therefore, in the present modification, the light converting member 130 and the diffusing member 180 can easily be disposed in the holding unit 140 like nesting.

Second Embodiment

A second embodiment of the present invention will be described below with reference to FIG. 6. In the present embodiment, only differences from the first embodiment will be described.

The holding unit 140 includes an engaging portion 151a, which is disposed between the holder entrance portion 161 and the holder exit portion 163 in the direction of the central axis C. Specifically, the engaging portion 151a is disposed between the first reflection member 120 and the light converting member 130 in the direction of the central axis C. The engaging portion 151a is disposed so as to be separated forward from the holder exit portion 163 by a relative distance. The engaging portion 151a is disposed on a planar region substantially orthogonal to the central axis C of the primary light and on the inner peripheral surface of the holding unit 140 in the third hollow portion 169. For example, the engaging portion 151a functions as a step portion on the tapered surface. For example, the engaging portion 151a is disposed all over the circumference of the inner peripheral surface and is shaped like a ring. The engaging portion 151a is included in the inner peripheral surface of the holding unit 140 in the third hollow portion 169. The outer diameter and the inner diameter of the engaging portion 151a are larger than the diameter of the holder entrance portion 161 and smaller than the diameter of the holder exit portion 163. The ring-shaped engaging portion 151a has an inner diameter that is smaller than the diameter of the light converting member 130. The engaging portion 151a is a plane that is substantially orthogonal to the central axis C. The engaging portion 151a may be disposed on at least part of the entire circumference of the inner peripheral surface. A second reflection member 200 is disposed in the engaging portion 151a.

The engaging portion 151a engages the light converting member 130 with the third hollow portion 169 so that the relative distance is maintained. At least a part of the engaging portion 151a, which is planar, is brought into contact with a part of the first surface 131 of the light converting member 130. Specifically, the first surface 131 is disposed in the engaging portion 151a so that the first surface 131 is separated from the holder entrance portion 161 by the relative distance. With this disposition, the peripheral end portion of the first surface 131 comes into contact with the engaging portion 151a and accordingly the light converting member 130 is engaged. The peripheral end portion is a portion of the first surface 131 excluding the second irradiation area 137, and is shaped like a ring and shows a part of the above-described first surface 131. The contact referred to herein indicates, for example, a surface contact, and the surface contact indicates, for example, that the entire opposing portion of the first surface 131, which is opposed to the engaging portion 151a, is brought into contact with the entire engaging portion 151a. In other words, the first surface 131 of the light converting member 130 is placed on the engaging portion 151a, and the engaging portion 151a supports the first surface 131. The engaging portion 151a thus engages at least a part of the orthogonal plane that is the first surface 131 of the light converting member 130 excluding the second irradiation area 137.

The engaging portion 151a includes a contact portion between a planar portion substantially orthogonal to the central axis C and a tapered surface of the holding unit 140. At this contact portion, the engaging portion 151a abuts on the outer peripheral edge of the first surface 131 of the light converting member 130. The engaging portion 15a thus functions as the orthogonal holding section 151. The engaging portion 151a need not abut on the entire circumference of the first surface 131 of the light converting member 130, but may abut on part thereof in the circumference direction.

When the light converting member 130 is engaged, the peripheral surface 135 of a first light converting member 50 is disposed apart from the inner peripheral surface of the holding unit 140 and the second reflection member 200. The second surface 133 of the light converting member 130 is disposed in the third hollow portion 169 away from the holder exit portion 163.

The shape of the engaging portion 151a is not particularly limited unless the engaging portion 151a blocks light traveling in the interior of the holding unit 140. The first surface 131 and the engaging portion 151a, which are in contact with each other, may be bonded to each other with an adhesive, for example. The adhesive is, for example, a transparent resin.

The third hollow portion 169 is shaped like a truncated cone gradually expanding toward the engaging portion 151a from the plane on which the first reflection member 120 is disposed in the direction of the central axis C. That is, in the direction of the central axis C and on the tapered surface extending from the first reflection member 120 to the engaging portion 151a, the inner diameter of the holding unit 140 gradually increases from the back (first reflection member 120) toward the front (engaging portion 151a) in the direction of the central axis C. As in the first embodiment, the second reflection member 200 is also disposed on the tapered surface. The engaging portion 151a is disposed outside (on the right and left sides of the drawing) the first reflection member 120 and the second reflection member 200 extending from the first reflection member 120 to the engaging portion 151a in a direction substantially orthogonal to the central axis C.

In the present embodiment, the light converting member 130 can stably be disposed in the holding unit 140 by the engaging portion 151a. Since the engaging portion 151a is substantially orthogonal to the central axis C, the central axis of the light converting member 130 can easily be disposed along the central axis C.

In the present embodiment, the engaging portion 151a is shaped like a ring, and is disposed outside (the right and left side of the drawing) the first reflection member 120 and the second reflection member 200. It is thus possible to prevent the engaging portion 151a from blocking light reflected forward by the first reflection member 120 and the second reflection member 200. Therefore, the illumination light can be emitted with efficiency and a desired quantity of light can be obtained.

The engaging portion 151a engages the light converting member 130, and may also engage the diffusing member 180 like the light converting member 130. The engaging portion 151a may be combined with the modification to the first embodiment.

Third Embodiment

Figure 7:
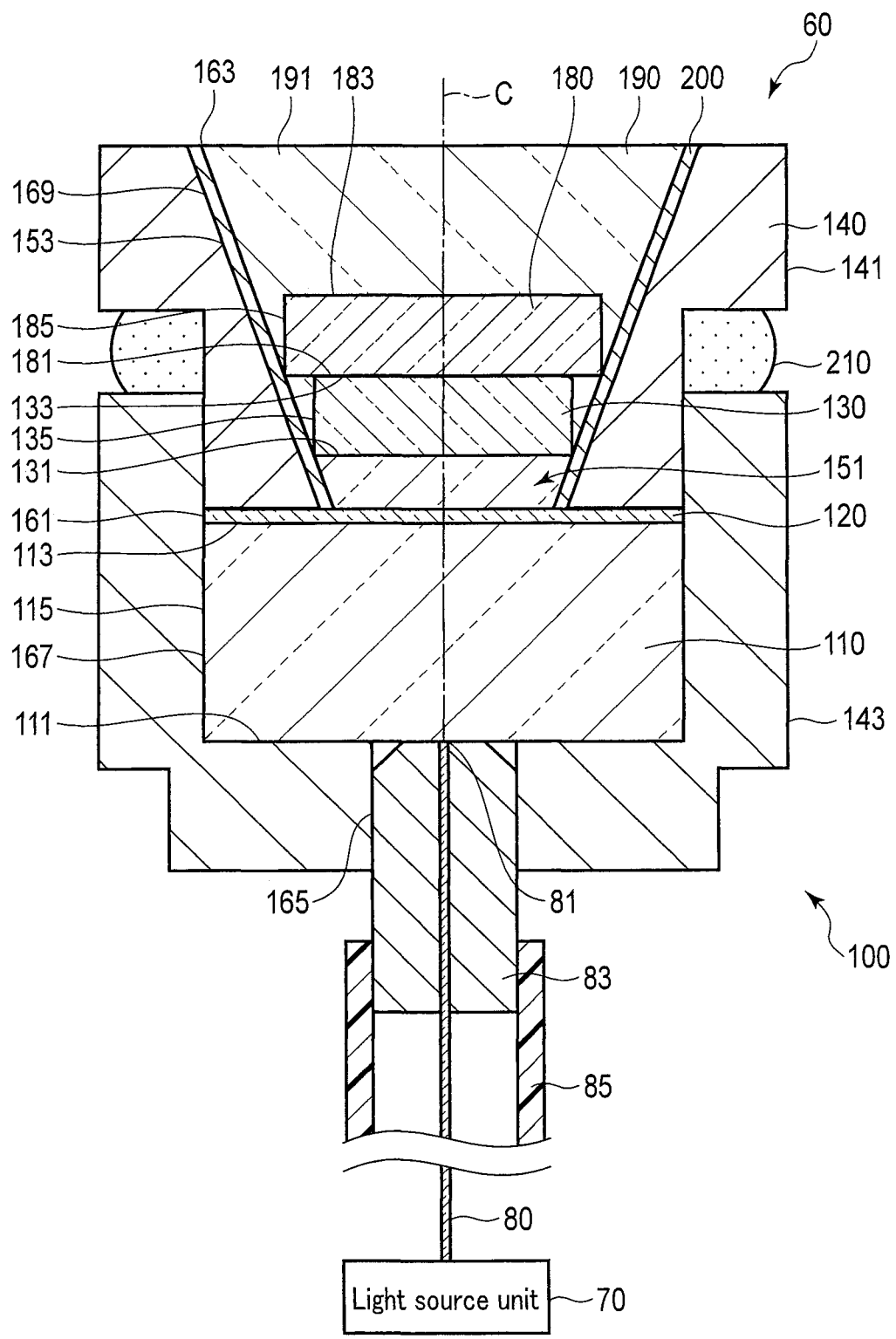
FIG. 7 is a diagram schematically showing an illumination device of a third embodiment.

A third embodiment of the present invention will be described below with reference to FIG. 7. In the present embodiment, only differences from the first embodiment will be described.

The holding unit 140 of the present embodiment includes a first holder 141 and a second holder 143 fixed to the first holder 141.

The first holder 141 includes a third hollow portion 169, and an orthogonal holding section 151, a light converting member 130, a diffusing member 180, a transparent member 190, a parallel holding section 153, a second reflection member 200, and a holder exit portion 163, which are arranged in the third hollow portion 169. The arrangement of the orthogonal holding section 151, light converting member 130, diffusing member 180, transparent member 190, parallel holding section 153, and second reflection member 200 is the same as that in the first embodiment.

The second holder 143 includes a first hollow portion 165, a second hollow portion 167, a transmission member 110, and a first reflection member 120 both arranged in the second hollow portion 167, and a holder entrance portion 161. The arrangement of the transmission member 110, first reflection member 120, and holder entrance portion 161 is the same as that in the first embodiment.

The diameter of the second hollow portion 167 is larger than the minimum diameter of the third hollow portion 169, and the diameter of each of the transmission member 110 and the first reflection member 120 is larger than the minimum diameter of the third hollow portion 169, the diameter of the light converting member 130 and the diameter of the diffusing member 180.

The first holder 141 is inserted into the second hollow portion 167 of the second holder 143, and the bottom surface of the first holder 141 is in close contact with the first reflection member 120 without any gap and is bonded to the first reflection member 120. The bottom surface is shaped like a ring and is disposed so as to surround the central axis C. Thus, the bottom surface does not block primary light that travels from the exit end face 81 to the light converting member 130. The periphery of the close-contact portion is surrounded by the peripheral surface of the second holder 143. The outer peripheral surface of the first holder 141 is bonded to the outer peripheral surface of the second holder 143 by, for example, an adhesive 210. The adhesive 210 is not positioned alongside the close-contact portion but is shifted to the close-contact portion in the direction of the central axis C. The adhesive 210 is disposed, for example, alongside the diffusing member 180.

The second holder 143 is a member through which the primary light, secondary light, or tertiary light is not transmitted. The member may reflect the primary light, secondary light, and tertiary light. The member is preferably nickel, brass, SUS, and the like. However, the member need not be limited to these metals.

The adhesive 210 is, for example, an epoxy adhesive or a silicone adhesive. The adhesive bonds by curing.

In the present embodiment, the orthogonal holding section 151, light converting member 130, diffusing member 180, transparent member 190, parallel holding section 153 and second reflection member 200 are disposed in the first holder 141, and the transmission member 110 and first reflection member 120 are disposed in the second holder 143. The first holder 141 is inserted into the second holder 143 and fixed to the second holder 143 by the adhesive 210. Thus, the first holder 141 and the second holder 143 can be assembled separately, and the illumination unit 100 can easily be assembled.

In the present embodiment, the bottom surface of the first holder 141 is in close contact with the first reflection member 120 without any gap, and is bonded to the first reflection member 120. It is thus possible to prevent return light, which returns to the first reflection member 120 from the front, from entering a gap and reduce loss of illumination light, with the result that a desired quantity of light can be obtained.

Fourth Embodiment

A fourth embodiment of the present invention will be described below with reference to FIG. 8. In the present embodiment, only differences from the first embodiment will be described.

The diffusing member 180 is disposed apart from the inner peripheral surface of the holding unit 140 so that at least part of at least one of the primary light and the secondary light can travel between the diffusing member 180 and the tapered surface that is the inner peripheral surface of the holding unit 140 in the third hollow portion 169. A gap is formed between the peripheral surface 185 and the inner peripheral surface of the diffusing member 180, and the transparent member 190 is disposed in the gap. For example, the diameter of the diffusing member 180 is substantially the same as that of the light converting member 130. The diameter of the diffusing member 180 may be greater than that of the light converting member 130.

For example, part of the primary light transmitted through the light converting member 130, part of the wavelength-converted light (secondary light) and part of the first diffused light (secondary light) diffused by the first diffusing member enter neither the diffusing member 180 nor the second reflection member 200 through the gap, but travel directly to the holder exit portion 163, without being diffused or reflected, and are emitted as illumination light. Although not shown, other part of the primary light, other part of the wavelength-converted light and other part of the first diffused light do not enter the diffusing member 180 but may be reflected toward the holder exit portion 163 by the second reflection member 200, without being diffused, may travel to the holder exit portion 163 and may be emitted as illumination light.

In the present embodiment, light that is decreased in its diffusion and scattering by the diffusing member 180 can be used as illumination light, and the quantity of light as illumination light can be increased.

Since the primary light is emitted as illumination light, it is necessary to, for example, adjust a light distribution balance between the primary light and the wavelength-converted light and set white light with less color unevenness as illumination light.

The present invention is not limited to the embodiments described above. When the invention is reduced to practice, its structural elements can be modified in different ways without departing from the spirit of the invention. The embodiments may be combined as appropriate as possible, and an advantageous effect can be obtained from the combination. The embodiments include inventions in a variety of stages, and a variety of inventions can be extracted by appropriate combinations of the structural elements of the embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An illumination device comprising:
 a light converter that primary light enters and that is configured to convert at least part of the primary light into secondary light having a second wavelength that differs from a first wavelength of the primary light and to diffuse the secondary light;

a first reflector configured to reflect at least part of the diffused secondary light toward the light converter; and a holder holding at least one of the first reflector and the light converter with the first reflector and the light converter being separated from each other so that the primary light transmitted through the first reflector enters the light converter.

2. The illumination device according to claim 1, wherein:
the first reflector is a reflection film;
a second reflectance of the reflection film to the second wavelength is higher than a first reflectance of the reflection film to the first wavelength; and
at least part of the primary light is transmitted through the first reflector and then enters the light converter.

3. The illumination device according to claim 1, wherein:
when an area of the first reflector that is irradiated with the secondary light traveling from the light converter toward the first reflector is defined as a first irradiation area and transmittance of the first reflector to the second wavelength of the secondary light is defined as secondary light transmittance, the holder holds the first reflector and the light converter so as to keep a relative distance between the light converter and the first reflector in accordance with an index value indicating a size of the first irradiation area and the secondary light transmittance.

4. The illumination device according to claim 3, wherein:
the first irradiation area is formed on a plane disposed along a direction that is substantially orthogonal to a direction of a central axis of the primary light traveling from the first reflector to the light converter; and
the index value is a radius of an approximate circle when the plane of the first irradiation area is shaped like an approximate circle, and the index value is a major axis radius of an approximate ellipse inscribed on the plane of the first irradiation area when the plane of the first irradiation area is shaped like a plane other than the approximate circle.

5. The illumination device according to claim 4, wherein:
the holder includes a holder exit portion that emits illumination light including the secondary light;
the light converter has a first surface that emits to the first reflector; and
the holder controls the relative distance so that the index value is less than a radius of the first surface of the light converter and so that the radius of the first surface of the light converter is less than a radius of the holder exit portion or substantially equal to the radius of the holder exit portion.

6. The illumination device according to claim 3, wherein:
when an incident angle of the secondary light that travels from the light converter with respect to the first reflector is α, the holder holds the first reflector and the light converter so that the relative distance is equal to or greater than a value obtained by dividing the index value by a tangent (tan α).

7. The illumination device according to claim 1, wherein:
the holder includes:
a holder entrance portion that the primary light enters and in which the first reflector is disposed; and
a holder exit portion that emits illumination light including the secondary light; and
the light converter is disposed on a side opposed to a light source unit configured to emit the primary light to the first reflector.

8. The illumination device according to claim 7, wherein:
the first reflector and the light converter have respective parallel surfaces that are substantially parallel to a direction of a central axis of the primary light traveling from the first reflector to the light converter; and
the holder includes a parallel holding section holding at least part of at least one of the parallel surfaces to control a relative distance between the light converter and the first reflector, the parallel holding section being included in an inner peripheral surface of the holder.

9. The illumination device according to claim 8, wherein:
the holder includes a hollow portion that communicates with the holder entrance portion and the holder exit portion and in which the light converter is disposed; and
an inner diameter of the holder in the hollow portion gradually increases from a plane on which the first reflector is located toward the holder exit portion in the direction of the central axis.

10. The illumination device according to claim 9, comprising
a second reflector that is disposed on at least part of the inner peripheral surface of the holder in the hollow portion, wherein:
the second reflector is disposed in the parallel holding section is configured to reflect light with which the second reflector is irradiated, toward the holder exit portion.

11. The illumination device according to claim 10, wherein:
the light converter converts the primary light into wavelength-converted light as the secondary light;
the wavelength-converted light is light having the second wavelength;
the second reflector reflects light that travels from the holder exit portion to the holder entrance portion, toward the holder exit portion; and
the light that travels from the holder exit portion to the holder entrance portion includes the wavelength-converted light that travels from the light converter to the holder entrance portion.

12. The illumination device according to claim 11, wherein:
the light converter further converts the primary light into first diffused light as the secondary light;
the first diffused light has a wavelength that is equal to the first wavelength of the primary light and has a light distribution angle that is different from a light distribution angle of the primary light; and
the light that travels from the holder exit portion to the holder entrance portion further includes the first diffused light that travels from the light converter to the holder entrance portion.

13. The illumination device according to claim 8, wherein:
the holder includes a first holder and a second holder fixed to the first holder;
the first holder includes a hollow portion, the light converter disposed in the hollow portion, and the holder exit portion;
the second holder includes the holder entrance portion;
the hollow portion communicates with the holder entrance portion and the holder exit portion; and
an inner diameter of the holder in the hollow portion gradually increases from a plane on which the first reflector is located toward the holder exit portion in the direction of the central axis.

14. The illumination device according to claim 7, wherein:
  each of the first reflector and the light converter has at least an orthogonal plane formed along a direction substantially orthogonal to a direction of a central axis of the primary light traveling from the first reflector to the light converter; and
  the holder includes an orthogonal holding section holding the orthogonal planes in order to control a relative distance between the light converter and the first reflector.

15. The illumination device according to claim 14, wherein:
  the holder includes an engaging portion that is disposed between the first reflector and the light converter in the direction of the central axis and that has an inner diameter that is smaller than a diameter of the light converter;
  the orthogonal plane of the light converter includes a second irradiation area irradiated with the primary light; and
  the engaging portion engages at least part of the orthogonal plane of the light converter excluding the second irradiation area.

16. The illumination device according to claim 15, wherein:
  the holder communicates with the holder entrance portion and the holder exit portion and includes a hollow portion in which the light converter is disposed; and
  an inner diameter of the holder in the hollow portion gradually increases from a plane on which the first reflector is located toward the engaging portion in the direction of the central axis.

17. The illumination device according to claim 15, wherein:
  the holder communicates with the holder entrance portion and the holder exit portion and includes a hollow portion in which the light converter is disposed; and
  the engaging portion is included in an inner peripheral surface of the holder in the hollow portion.

18. The illumination device according to claim 1, comprising
  a diffusing member, the diffusing member being disposed on a side opposed to the first reflector with respect to the light converter, at least part of the diffusing member being disposed on a central axis of the primary light traveling from the first reflector to the light converter, and the diffusing member diffusing at least part of light with which the diffusing member is irradiated, by increasing a spread angle of the light without changing a wavelength of the light.

19. The illumination device according to claim 18, wherein:
  the holder includes a hollow portion in which the light converter and the diffusing member are disposed; and
  the diffusing member is disposed apart from the inner peripheral surface so that at least part of at least one of the primary light and the secondary light is allowed to travel between the diffusing member and the inner peripheral surface of the holder in the hollow portion.

20. An endoscope apparatus comprising:
  a light converter that primary light enters and that is configured to convert at least part of the primary light into secondary light having a second wavelength that differs from a first wavelength of the primary light and to diffuse the secondary light;
  a first reflector configured to reflect at least part of the diffused secondary light toward the light converter;
  a holder holding at least one of the first reflector and the light converter with the first reflector and the light converter being separated from each other so that the primary light transmitted through the first reflector enters the light converter; and
  an endoscope configured to emit illumination light generated based on the primary light.

* * * * *